(12) United States Patent
Hildebrandt et al.

(10) Patent No.: US 9,127,020 B2
(45) Date of Patent: *Sep. 8, 2015

(54) EVAPORABLE ORGANIC SEMICONDUCTIVE MATERIAL AND USE THEREOF IN AN OPTOELECTRONIC COMPONENT

(75) Inventors: Dirk Hildebrandt, Neu-Ulm (DE); Gunter Mattersteig, Ulm (DE); Olga Gerdes, Ulm (DE); Serge Vetter, Ulm (DE); Andre Weiss, Ulm (DE)

(73) Assignee: HELIATEK GMBH, Dresden (DE)

( * ) Notice: Subject to any disclaimer, the term of this patent is extended or adjusted under 35 U.S.C. 154(b) by 316 days.
This patent is subject to a terminal disclaimer.

(21) Appl. No.: 13/805,568

(22) PCT Filed: Jun. 24, 2011

(86) PCT No.: PCT/EP2011/060668
§ 371 (c)(1),
(2), (4) Date: Mar. 8, 2013

(87) PCT Pub. No.: WO2011/161262
PCT Pub. Date: Dec. 29, 2011

(65) Prior Publication Data
US 2013/0167930 A1    Jul. 4, 2013

(30) Foreign Application Priority Data
Jun. 24, 2010    (DE) .......................... 10 2010 030 500

(51) Int. Cl.
*C07D 519/00* (2006.01)
*C07D 495/04* (2006.01)
(Continued)

(52) U.S. Cl.
CPC ............... *C07D 495/14* (2013.01); *B82Y 10/00* (2013.01); *C07D 409/14* (2013.01);
(Continued)

(58) Field of Classification Search
CPC .. C07D 519/00; C07D 495/04; C07D 409/14; C07D 417/14; C07D 495/14; C07D 513/14; H01L 51/0071; H01L 51/0074
See application file for complete search history.

(56) References Cited

U.S. PATENT DOCUMENTS

| 7,655,809 B2 | 2/2010 | Fallis et al. |
| 2003/0021912 A1 | 1/2003 | Farrand et al. |

(Continued)

FOREIGN PATENT DOCUMENTS

| DE | 60205824 T2 | 5/2006 |
| EP | 1275651 B1 | 8/2005 |

(Continued)

OTHER PUBLICATIONS

Odom, Susan A.; Lancaster, Kelly; Beverina, Luca; Lefler, Kelly M., Thompson, Natalie J., Coropceanu, Veaceslav; Brédas, Jean-Luc; Marder, Seth R.; Barlow, Stephen,. Bis[bis-(4-alkoxyphenyl)amino] Derivatives of Dithienylethene, Bithiophene, Dithienothiophene and Dithienopyrrole: Palladium-Catalysed Synthesis and Highly Delocalised Radical Cations. *Chem. Eur. J. 2007*, 13, 9637-9464.

(Continued)

*Primary Examiner* — Matthew Coughlin
(74) *Attorney, Agent, or Firm* — Heslin Rothenberg Farley & Mesiti P.C.

(57) ABSTRACT

The invention relates to compounds of general formula IIIa and their use in optoelectronic components.

Figure 1:
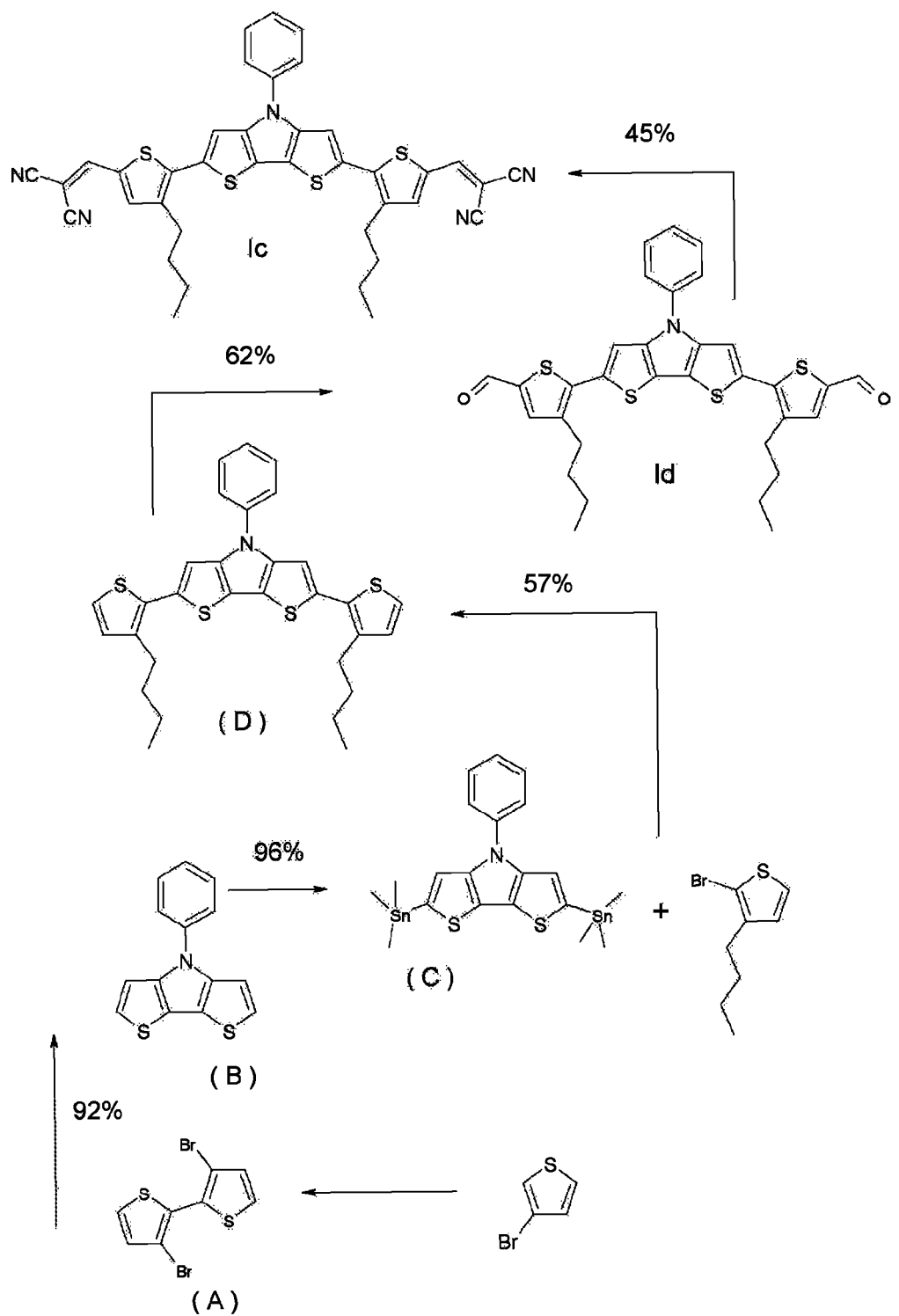

IIIa:

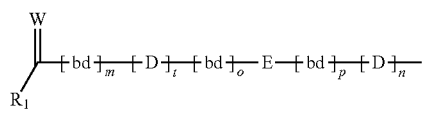

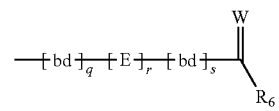

20 Claims, 12 Drawing Sheets

(51) Int. Cl.

| | |
|---|---|
| C07D 409/14 | (2006.01) |
| C07D 417/14 | (2006.01) |
| C07D 495/14 | (2006.01) |
| C07D 513/14 | (2006.01) |
| H01L 51/00 | (2006.01) |
| B82Y 10/00 | (2011.01) |
| C07D 498/04 | (2006.01) |
| H01L 51/42 | (2006.01) |

(52) U.S. Cl.
CPC ........... *C07D 417/14* (2013.01); *C07D 495/04* (2013.01); *C07D 498/04* (2013.01); *C07D 513/14* (2013.01); *C07D 519/00* (2013.01); *H01L 51/0062* (2013.01); *H01L 51/0065* (2013.01); *H01L 51/0068* (2013.01); *H01L 51/0071* (2013.01); *H01L 51/0074* (2013.01); *H01L 51/001* (2013.01); *H01L 51/0046* (2013.01); *H01L 51/4253* (2013.01)

(56) References Cited

U.S. PATENT DOCUMENTS

| | | |
|---|---|---|
| 2007/0112171 A1 | 5/2007 | Li et al. |
| 2013/0167931 A1 | 7/2013 | Hildebrandt et al. |

FOREIGN PATENT DOCUMENTS

| | | | |
|---|---|---|---|
| EP | 2072557 A1 | | 6/2009 |
| EP | 2192159 A2 | * | 6/2010 |
| JP | 2013532384 | | 8/2013 |
| WO | WO 2006/092134 A1 | | 9/2006 |
| WO | WO 2006/111511 A1 | | 10/2006 |
| WO | WO 2007/116001 A2 | | 10/2007 |
| WO | WO 2008/088595 A2 | | 7/2008 |
| WO | WO 2008/145172 A1 | | 12/2008 |
| WO | WO 2009/051390 A2 | | 4/2009 |
| WO | WO 2010/079064 A2 | | 7/2010 |

OTHER PUBLICATIONS

Barlow, Stephen; Zhang, Qing; Kaafarani, Bilal R.; Risko, Chad; Amy, Fabrice; Chan, Calvin K.; Domercq, Benoit; Starikova, Zoya A.; Antipin, Mikhail Yu; Timofeeva, Tatiana V.; Kippelen, Bernard; Brédas, Jean-Luc; Kahn; Marder, Seth R. Synthesis, Ionisation Potentials and Electron Affinities of Hexaazatrinaphthylene Derivatives. *Chem Eur J. 2007*, 13, 3537-3547.
Belen'kii, L.I.; Shirinyan, V.Z.; Gromova, G.P.; Kolotaev, A.V.; Strelenko, Yu.A.; Tandura, S.N.; Shumskii, A.N.; Krayushkin, M.M. A New Approach to the Synthesis of Dithienylethanediones and Dithienylacetylenes. *Chemistry of Heterocyclic Compounds*, vol. 39, No. 12, 2003.
Bodea, Cornel; Raileanu, Metodiu. Brom-Phenthiazine Und Brom-Phenthiazone. *Chemical Institute of the Romanian Academy*, Oct. 9, 1959.
Reynolds, John R. A New, Improved and Convenient Synthesis of 4*H*-Cyclopenta[2,1-*b*:3,4-*b*']-dithiophen-4-one. *Synthesis 2002*, No. 8, Apr. 6, 2002.
Cai, Xiuyu; Burand, Michael W.; Newman, Christopher R.; da Silva Filho, Demetrio A.; Pappenfus, Ted M.; Bader, Mamoun M.; Brédas, Jean-Luc; Mann, Kent R.; Frisbie, C. Daniel. N- and P-Channel Transport Behavior in Thin Film Transistors Based on Tricyanovinyl-Capped Oligothiophenes. *J. Phys. Chem. D 2006*, 110, 14590-14597.
Dietsche, Thomas A.; Gorman, David B.; Orvik, Jon A.; Roth, Gary A.; Shiang, William R. Process Chemistry Related to the Experimental Rice Herbicide 2,2-Dimethyl-1-(4-methylthio-5-pyrimidinyl) indane. *Organic Process Research & Development 2000*, 4, 275-285.
Frère, Pierre; Raimundo, Jean-Manuel; Blanchard, Philippe; Delaunay, Jacques; Richomme, Pascal; Sauvajol, Jean-Louis; Orduna, Jesus; Garin, Javier; Roncali, Jean. Effect of Local Molecular Structure on the Chain-Length Dependence of the Electronic Properties of Thiophene-Based π-Conjugated Systems. *J. Org. Chem. 2003*, 68, 7254-7265.
Getmanenko, Yulla A.; Tongwa, Paul; Timofeeva, Tatiana V.; Marder, Seth R. Base-Catalyzed Halogen Dance Reaction and Oxidative Coupling Sequence as a Convenient Method for the Preparation of Dihalo-bisheteroarenes. *Organic Letters 2010*, vol. 12, No. 9, 2136-2139.
Syntheses of Thiophenes with Group V Substituents, Nitrogen Derivatives.
Bi-, Ter- and Oligothienyls, Unsymmetrical Bithienyls.
Hou, Jianhui; Park, Mi-Hyae; Zhang, Shaoqing; Yao, Yan; Chen, Li-Min; Li, Juo-Hao; Yang, Yang. Bandgap and Molecular Energy Level Control of Conjugated Polymer Photovoltaic Materials Based on Benzol[1,2-*b*:4, 5-*b*']dithiophene. *Macromolecules 2008*, 41, 6012-6018.
Xue, Jiangeng; Uchida, Soichi; Rand, Barry P., Forrest, Stephen R. Asymmetric tandem organic photovoltaic cells with hybrid planar-mixed molecular heterojunctions. *Applied Physics Letters*, vol. 85, No. 23.
Jorgensen, Mikkel; Krebs, Frederick C.; Bechgaard, Klaus Easy Access to 3,8-Diaryldifurano[2,3-*a*:2',3'-*f*]naphthalenes. A New Extended Aromatic System. *J. Org. Chem. 2000*, 65, 8783-8785.
Laquindanum, Joyce G.; Katz, Howard E.; Lovinger, Andrew J.; Dodabalapur, Ananth. Benzodithiophene Rings as Semiconductor Building Blocks. *Adv. Mater. 1997*, 9, No. 1.
Liu, Junying; Zhang, Rui; Osaka, Itaru; Mishra, Sarada; Javier, Anna E.; Smilgies, Detlef-M.; Kowalewski, Tomasz; McCullough, Richard D. Transistor Paint: Evironmentally Stable *N*-alkyldithienopyrrole and Bithiazole-Based Copolymer Thin-Film Transistors Show Reproducible High Mobilities without Annealing. *Adv. Funct. Mater. 2009*, 19, 3427-3434.
Oka, Hiroyuki, Synthesis and through-bond spin interaction of stable 1, 3-phenylene linked poly(phenothiazine cation radical). *J. Mater. Chem.*, 2008, 18, 1927-1934|1927.
O' Regan, Brian; Grätzel, Michael. A low-cost, high-efficiency solar cell based on dye-sensitized colloidal $TiO_2$ films. *Nature*, vol. 353, Oct. 24, 1991.
D.5.1. Elektrophile aromatische Substitution.
D.5. Substitutionem an Aromaten.
Pappenfus, Ted M.; Hermanson, Bethany J.; Helland, Tyler J.; Lee, Garrett G.W.; Drew, Steven M.; Mann, Kent R.; McGee, Kari A.; Rasmussen Seth C. Reduced Band Gap Dithieno[3,2-*b*:2',3'-*d*]pyrroles: New n-Type Organic Materials via unexpected Reactivity. *Organic Letters 2008*, vol. 10, No. 8, 1553-1556.
3-(2-Furyl)Acrylonitrile. *Organic Syntheses, Coll.* vol. 5, p. 585 (1973); vol. 40, p. 46 (1960).
Pfeiffer, Martin. Controlled Doping of Organic Vacuum Deposited Dye Layers: Basics and Applications. Dresden 1999, *Institute of Applied Photophysics*.
Qi, Ting; Liu, Yunqi; Qiu, Wenfeng; Zhang, Hengjun; Gao, Xike; Liu, Ying; Lu, Kun; Du, Chunyan; Yu, Gui; Zhu, Daoben. Synthesis and properties of fluorine or carbazole-based and dicyanovinyl-capped n-type organic semiconductors, J. Mater. Chem. 2008, 18, 1131-1138 | 1131.
Ogawa, Katsu; Radke, Karla R.; Rothstein Scott D.; Rasmussen, Seth C. Synthesis of Secondary and Tertiary Aminothiophenes via Palladium-Catalyzed Amination. *J. Org. Chem. 2001*, 66, 9067-9070.
Sahu, Duryodhan; Padhy, Harihara; Patra, Dhananjaya; Yin, Jen-Fu; Hsu, Ying-Chan; Lin, Juann-T'Suen; Lu, Kuang-Lieh; Wei, Kung-Hwa; Lin, Hong-Cheu. Synthesis and applications of novel acceptor-donor-acceptor organic dyes with dithienopyrrole- and fluorine-cores for dye-sensitized solar cells. *Tetrahedron 67* (2011) 303-311.
Shinamura, Shoji; Miyazaki, Eigo; Takimiya, Kazuo. Synthesis, Properties, Crystal Structures, and Semiconductor Characteristics of Napthol[1,2-*b*:5,6-*b*']dithiophene and -diselenophene Derivatives. *J. Org. Chem. 2010*, 75, 1228-1234.
Sirringhaus, Henning; Friend, Richard H.; Wang, Changsheng; Leuninger, Jörg; Müllen, Klaus. Dibenzothienobisbenzothiophene—a novel fused-ring oligomer with high field-effect mobility. *J. Mater. Chem.*, 1999, 9, 2095-2101.

(56) References Cited

OTHER PUBLICATIONS

Song, Changsik; Walker, D. Barney; Swager, Timothy M. Conducting Thiophene-Annulated Azepine Polymers. *Macromolecules 2010*, 43, 5233-5237.

Stangeland, Eric L.; Sammakia, Tarek. Use of Thiazoles in the Halogen Dance Reaction: Application to the Total Synthesis of WS75624 B. *J. Org. Chem. 2004,* 69, 2381-2385.

Tang, C. W., Two-layer organic photovoltaic cell. Appl. Phys. Lett. 48(2), Jan. 13, 1986.

Usta, Hakan; Lu, Gang; Facchetti, Antonio; Marks, Tobin J. Dithienosilole- and Dibenzosilole-Thiophene Copolymers as Semiconductors for Organic Thin-Film Transistors. *J. Am. Chem. Soc. 2006*, 128, 9034-9035.

Yassin, Ali; Rousseah, Theodulf; Leriche, Philippe; Cravino, Antonio; Roncali, Jean Evaluation of bis-dicyanovinyl short-chain conjugated systems as donor materials for organic solar cells. *Sol. Energy Mater. Sol. Cells* (2010), doi: 10.1016/j.solmat.2010.08.032.

Berlin, Anna; Pagani, Giorgio. Electrochemical polymerization of 1$H$, 7$H$-pyrrolo[2',3':4,5]-thieno[3,2-$b$]pyrrole and 4$H$-dithieno[3,2-$b$;2'3'-$d$]pyrrole. Makromol. Chem. 193, 399-409 (1992).

\* cited by examiner

EVAPORABLE ORGANIC SEMICONDUCTIVE MATERIAL AND USE THEREOF IN AN OPTOELECTRONIC COMPONENT

The invention relates to an organic semiconductive material of the general formulae I and II, and also IIIa.

Research and development in organic solar cells has increased significantly, particularly in the last ten years. The maximum efficiency reported to date for what are called "small molecules" is 5.7% [Jiangeng Xue, Soichi Uchida, Barry P. Rand, and Stephen R. Forrest, Appl. Phys. Lett. 85 (2004) 5757]. Small molecules are understood in the context of the present invention to mean nonpolymeric organic monodisperse molecules in the mass range between 100 and 2000 grams/mol. These have to date been unable to achieve the efficiencies of 10-20% typical of inorganic solar cells. Organic solar cells, however, are subject to the same physical limitations as inorganic solar cells, and therefore, at least theoretically, similar efficiencies are to be expected after corresponding development work.

Organic solar cells consist of a sequence of thin layers (each typically of thickness 1 nm to 1 μm) of organic materials which are preferably vapor-deposited under reduced pressure or spun on from a solution. Electrical contacting can be effected by means of metal layers, transparent conductive oxides (TCOs) and/or transparent conductive polymers (PEDOT-PSS, PANI).

A solar cell converts light energy to electrical energy. In this context, the term "photoactive" is understood to mean the conversion of light energy to electrical energy. In contrast to inorganic solar cells, the light does not directly generate free charge carriers in organic solar cells, but excitons are instead first formed, i.e. electrically neutral excited states (bound electron-hole pairs). Only in a second step are these excitons separated into free charge carriers, which then contribute to electrical current flow.

The advantage of such organic-based components over the conventional inorganic-based components (semiconductors such as silicon, gallium arsenide) is that the optical absorption coefficients are in some cases extremely high (up to $2\times10^5$ cm$^{-1}$), and these allow production of efficient absorber layers of only a few nanometers in thickness, such that it is possible to produce very thin solar cells with low material consumption and energy expenditure. Further technological aspects are the low costs, the organic semiconductor materials used being very inexpensive in the case of production in relatively large amounts, the possibility of producing flexible large-area components on plastic films, and the virtually unlimited possible variations and the unlimited availability of organic chemistry.

Since high temperatures are not required in the production process, it is possible to produce organic solar cells as components both flexibly and over a large area on inexpensive substrates, for example metal foil, plastic film or polymer fabric. This opens up new fields of use which remain closed to the conventional solar cells. Due to the virtually unlimited number of different organic compounds, the materials can be tailored to their respective task.

One possible implementation of an organic solar cell which has already been proposed in the literature is that of a pin diode [Martin Pfeiffer, "Controlled doping of organic vacuum deposited dye layers: basics and applications", PhD thesis TU-Dresden, 1999] with the following layer structure:
0. Carrier, substrate,
1. Base contact, usually transparent,
2. p layer(s),
3. i layer(s),
4. n layer(s),
5. Top contact.

In this context, n and p mean n- and p-doping respectively, this leading to an increase in the density of, respectively, free electrons and holes in the thermal equilibrium state. In this context, such layers are understood primarily to be transport layers. The term i layer, in contrast, refers to an undoped layer (intrinsic layer). One or more i layer(s) in this context layers may consist either of one material or of a mixture of two materials (called interpenetrating networks). In contrast to inorganic solar cells, the charge carrier pairs in organic semiconductors, however, are not in free form after absorption, but form a quasi-particle, called an exciton, due to the lower attenuation of mutual attraction. In order to make the energy present in the exciton utilizable as electrical energy, this exciton has to be separated into free charge carriers. Since sufficiently high fields for separation of the excitons are not available in organic solar cells, the exciton separation is conducted at photoactive interfaces. The photoactive interface may take the form of an organic donor-acceptor interface [C. W. Tang, Appl. Phys. Lett. 48 (1986) 183] or of an interface to an inorganic semiconductor [B. O'Regan, M. Grätzel, Nature 1991, 353, 737])]. The excitons diffuse to such an active interface, where electrons and holes are separated from one another. This may be between the p (n) layer and the i layer, or between two i layers. In the installed electrical field of the solar cell, the electrons are then transported away to the n region and the holes to the p region. The transport layers are preferably transparent or substantially transparent materials with a wide band gap. Wide-gap materials refer here to materials whose absorption maximum is in the wavelength range of <450 nm, preferably at <400 nm.

Since the light always first produces excitons and no free charge carriers as yet, the low-recombination diffusion of excitons to the active interface plays a critical role in organic solar cells. In order to make a contribution to the photocurrent, the exciton diffusion length in a good organic solar cell must therefore significantly exceed the typical penetration depth of light in order that the predominant portion of the light can be utilized. Thin layers or organic crystals perfect in terms of structure and with regard to chemical purity do indeed meet this criterion. For large-area applications, however, the use of monocrystalline organic materials is impossible and the production of multiple layers with sufficient structural perfection is still very difficult to date.

An important factor in the improvement of the abovementioned solar cells lies in the further development of the organic layers. For the absorber layers, specifically in the field of small molecules, few novel materials have become known in the last 5 years.

WO2006092134A1 discloses compounds which have an acceptor-donor-acceptor structure, the donor block having an extensive Π system.

DE60205824T2 discloses thienothiophene derivatives which form a Π system with further aromatic rings and are framed on both sides by alkyl groups, and the use thereof in organic semiconductors.

WO2009051390 discloses thiophene-based acceptor-donor dyes for use in dye-sensitive solar cells.

WO 002008145172A1 presents novel phthalocyanines for use in solar cells.

U.S. Pat. No. 7,655,809B2 discloses compounds composed of 5 fused carbocycles in series and the use thereof as organic semiconductors.

WO 2006111511A1 and WO2007116001A2 disclose rylenetetracarboxylic acid derivatives for use as an active layer in photovoltaics.

In contrast, various polymers are known for use as active layers in organic photovoltaics, for example disclosed in WO 2008088595A2, EP2072557A1 or US 2007011217A1. These are generally not vaporizable, and are instead processed in liquid form to thin layers.

In the last 3 years, as a result of the various approaches, regular improvements in efficiencies for organic solar cells have been reported. Nevertheless, the efficiencies currently achieved are still insufficient for commercial use.

It is an object of the invention to provide a material which is vaporizable under reduced pressure and can be used as a light absorber in an organic solar cell. It is a further object of the invention to specify an optoelectronic component which comprises an organic vaporizable semiconductor material which overcomes the disadvantages mentioned in the prior art.

In accordance with the invention, this object is achieved by compounds of the general formula IIIa:

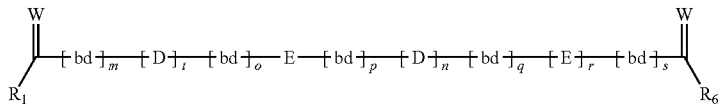

where each W is independently selected from C(CN)$_2$, CHCN, C(CN)COOR' where R' is in each case selected from C1-C10 alkyl, C3-C10 aryl and C2-C8 heteroaryl, more preferably selected from C(CN)$_2$, CHCN, R$_1$ and R$_6$ are each independently selected from H, C1-C30 alkyl, C1-C30 perfluoroalkyl, C3-C10 aryl, C2-C8-heteroaryl, CN, where the D groups are selected from:

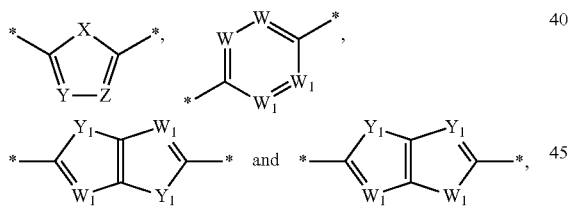

where Y$_1$ is selected from: O, S, Se, P(R), P(O)R, Si(RR'), C(RR') and N(R) and W$_1$ is independently selected from: N and C—R where R and R' are each independently selected from substituted and unsubstituted C1 to C30 alkyl, C3-C6 aryl and C3-C8 heteroaryl and where each X is selected independently from O, NR', S, Se, where R' is selected from C1-C30 alkyl, C1-C10 aryl and C1-C8 heteroaryl, each Y is independently selected from N and CR9 where R9=H, halogen, C1-C30 alkyl, C1-C30 alkenyl, C1-C30 alkynyl, each linear or branched, substituted or unsubstituted, OR', SR', SiR'$_3$, NR'$_2$, where R' is selected from C1-C10 alkyl, C3-C10 aryl and C1-C8 heteroaryl, each Z is independently selected from N and CR10 where R10=H, halogen, C1-C30 alkyl, C1-C30 alkenyl, C1-C30 alkynyl, each linear or branched, substituted or unsubstituted, OR', SR', SiR'$_3$, NR'$_2$, where R' is selected from C1-C10 alkyl, C3-C10 aryl and C1-C8 heteroaryl, where the E groups are selected from:

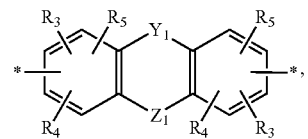

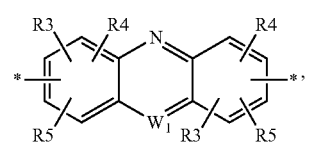

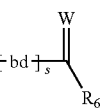

-continued

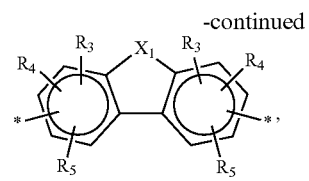

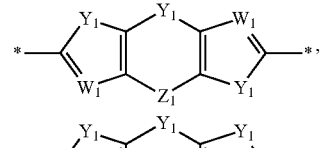

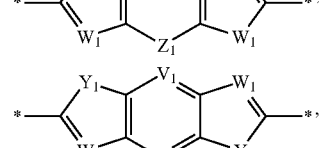

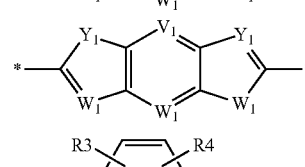

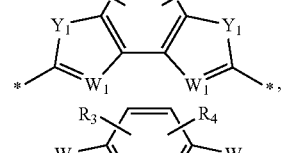

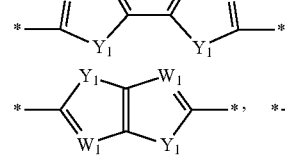

-continued

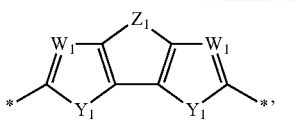

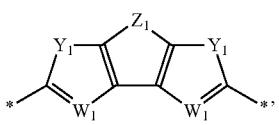

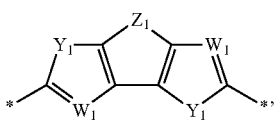

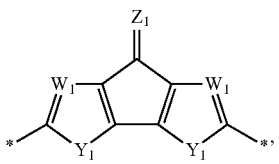

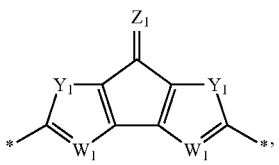

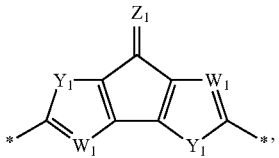

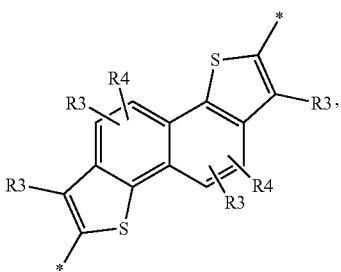

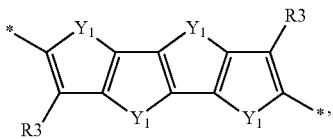

-continued

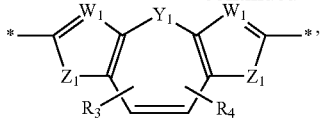

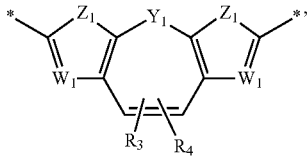

where $V_1$ and $W_1$ are each independently selected from:
N and C—R where R=H, halogen, C1-C30 alkyl, C1-C30 alkenyl, C1-C30 alkynyl, each linear or branched, substituted or unsubstituted, C3-C10 aryl or C1-C8 heteroaryl, substituted or unsubstituted, halogen, OR', SR', SiR'$_3$, NR'$_2$, where R' is selected from C1-C10 alkyl, C1-C10 aryl and C1-C8 heteroaryl, $V_1$ and $W_1$ preferably each independently being selected from: N and C—R where R=H, halogen, C1-C30 alkyl, C1-C30 alkenyl, C1-C30 alkynyl, each linear or branched, substituted or unsubstituted, C3-C10 aryl or C1-C8 heteroaryl, substituted or unsubstituted, OR', SR', SiR'$_3$, NR'$_2$, where R' is selected from C1-C10 alkyl, C1-C10 aryl and C1-C8 heteroaryl, $Y_1$ and $Z_1$ are each selected from: O, S, Se, P(R), P(O)R, Sr(RR'), C(RR') and N(R), where R and R' are each independently selected from H, linear or branched, substituted or unsubstituted C1-C30 alkyl, substituted or unsubstituted aryl, substituted or unsubstituted heteroaryl, acyl (COR'), COOR' and OR', where R' is selected from C1-C30 alkyl, C3-C10 aryl and C1-C8 heteroaryl, $Y_1$ and $Z_1$ preferably each being selected from: O, S, Se, Si(RR'), C(RR') and N(R), where R and R' are each independently selected from H, linear or branched, substituted or unsubstituted C1-C30 alkyl, substituted or unsubstituted aryl, substituted or unsubstituted heteroaryl, acyl (COR'), COOR' and OR', where R' is selected from C1-C30 alkyl, C3-C10 aryl and C1-C8 heteroaryl, and $X_1$ is selected from: O, S, Se, P(R), P(O)R and Si(RR'), and R and R' are each independently selected from H, C1 to C20 alkyl, linear or branched, substituted or unsubstituted, C3 to C6 aryl or C3 to C8 heteroaryl, OR', SR', SiR'3, NR'2, where R' is selected from C1-C10 alkyl, C3-C6 aryl and C3-C8 heteroaryl, $X_1$ preferably being selected from O, S, Se and Si(RR'), and R and R' each independently being selected from H, C1 to C20 alkyl, linear or branched, substituted or unsubstituted, C3 to C6 aryl or C3 to C8 heteroaryl, OR', SR', SiR'3, NR'2, where R' is selected from C1-C10 alkyl, C3-C6 aryl and C3-C8 heteroaryl, and where R3, R4 and R5 are each independently H, C1 to C20 alkyl, linear or branched, substituted or substituted, C3 to C6 aryl or C3 to C8 heteroaryl, OR', SR', SiR'3, NR'2, where R' may be selected from C1-C10 alkyl, C3-C6 aryl and C3-C8 heteroaryl, bd is independently *—C=C—* or *—C≡C—*, n, m, o, p, q, and r, s and t may each independently be 0 or 1, with the proviso that at least one parameter is 1, and where one donor unit formed from the groups bd, E and D has at least 10 conjugated electrons and the bonds identified with the asterisk* indicate the bonds to further groups in the compounds.

The inventive compounds are preferably symmetric in relation to the main chain, i.e. have identical units D and E and, if present, identical double or triple bonds bd, where substituents on the main chain may be different. More particularly, the inventive compounds have either point or mirror symmetry in relation to the main chain. Such symmetric compounds take on an ordered layer alignment in optoelectronic components and are therefore particularly suitable as active layers in these components.

In a further preferred embodiment, the compounds are symmetric not just with respect to the main chain but also with respect to the substituents on the main chain, for example alkyl groups or ether groups.

Further preferably, the donor unit formed from the D, E and bd groups has at least 12 conjugated electrons.

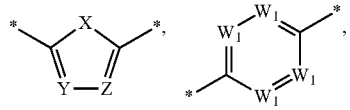

where the parameters $r=s=0$.

In addition, the E group may be

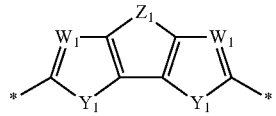

where $Y_1=S$ and the D groups may be

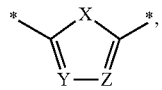

so as to result in compounds having the general formula:

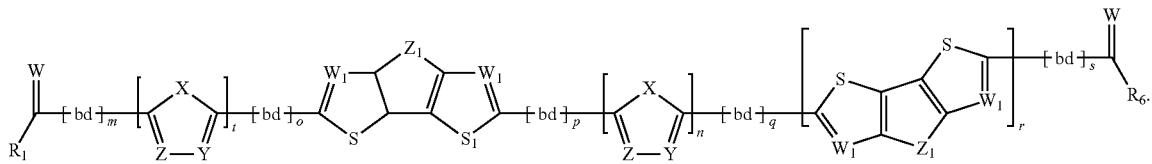

The inventive compounds are oligomers and have good vaporizability from vacuum. These compounds have two electron acceptor blocks

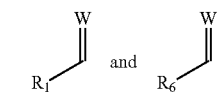

which flank an extensive electron donor block formed from the D, E and bd groups.

In a further embodiment of the invention, the compounds have a D group selected from In a further variant of the abovementioned general formula, the compounds have the parameters m, r, s and $q=0$ with the general formula:

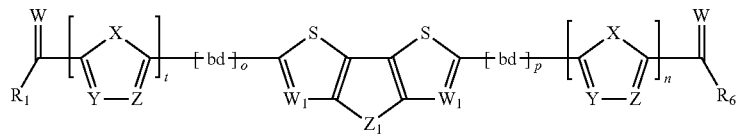

In addition, these compounds where o and $p=0$ and t and $n=1$ and $W_1=C-R$ may be representable by the general formula:

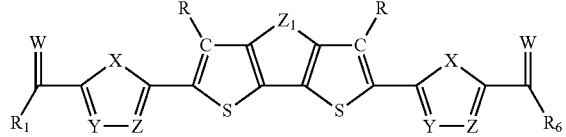

The compounds with the parameters t, m, o and $s=0$ and $r=1$ may be described by the general formula:

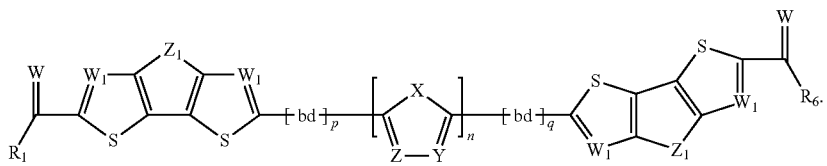

This general formula can be converted by the selection of the parameters p and q=0 and $W_1$=C—R to the following more specific formula:

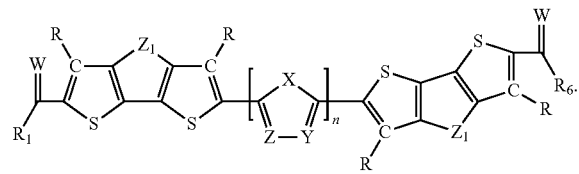

Alternatively, the inventive compounds may have the groups

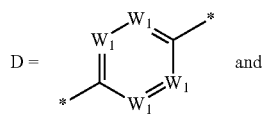

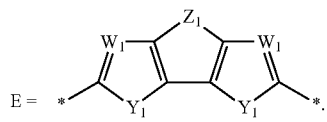

Such compounds where m, r, s and q=0 and t and n each=1 may be represented by the general formula:

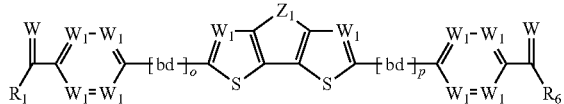

where preferably the parameters o and p=0 and $W_1$=C—R.

Further compounds may have the groups

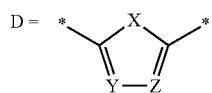

and E selected from:

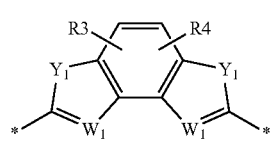

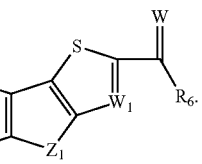

These compounds may have the parameters m, q, r and s=0 and t and n each=1 with the general formula:

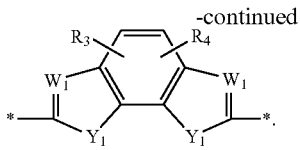

where, more particularly, X may be S and $Y_1$ may be S, and $W_1$ may be C—R.

Further alternative compounds have the parameters m, t, n, o, q, s=0 and r=1, where E is selected from:

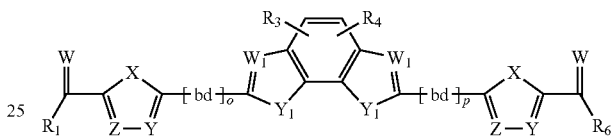

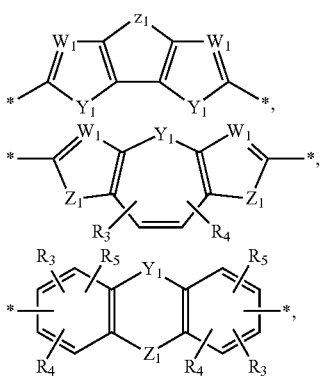

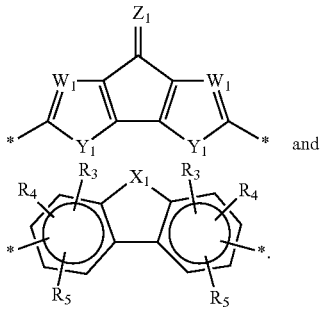

In these compounds, p may additionally be 0.

The electron acceptor groups preferably have mono-, di-, or tricyanovinylene groups, where W is selected from: $C(CN)_2$, CHCN, and R1 and R6 are selected from: H and CN.

A further embodiment of the invention provides compounds of the general formula I or II

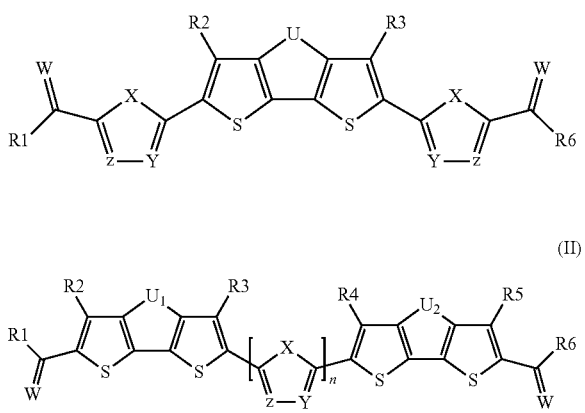

where U, U1 and U2 are each independently selected from N—R7, SiR7R8, CR7R8, where R7 and R8 are each independently selected from H, linear or branched, substituted or unsubstituted C1-C30 alkyl, substituted or unsubstituted aryl, substituted or unsubstituted heteroaryl, acyl (COR'), COOR' and OR', where R' is selected from C1-C30 alkyl, C3-C10 aryl and C1-C8 heteroaryl, R2, R3, R4 and R5 are each independently selected from H, halogen, C1-C30 alkyl, C1-C30 alkenyl, C1-C30 alkynyl, each linear or branched, substituted or unsubstituted, C3-C10 aryl or C1-C8 heteroaryl, substituted or unsubstituted, OR', SR', SiR'$_3$, NR'$_2$, where R' is selected from C1-C10 alkyl, C1-C10 aryl and C1-C8 heteroaryl, each X is independently selected from O, NR', S, Se, where R' is selected from C1-C30 alkyl, C1-C10 aryl and C1-C8 heteroaryl, each Y is independently selected from N and CR9, where R9=H, halogen, C1-C30 alkyl, C1-C30 alkenyl, C1-C30 alkynyl, each linear or branched, substituted or unsubstituted, OR', SR', SiR'$_3$, NR'$_2$, where R' is selected from C1-C10 alkyl, C1-C10 aryl and C1-C8 heteroaryl, each Z is independently selected from N and CR10, where R10=H, halogen, C1-C30 alkyl, C1-C30 alkenyl, C1-C30 alkynl, each linear or branched, substituted or unsubstituted, OR', SR', SiR'$_3$, NR'$_2$, where R' is selected from C1-C10 alkyl, C1-C10 aryl and C1-C8 heteroaryl, R1 and R6 are each independently selected from H, C1-C30 alkyl, C1-C30 perfluoroalkyl, C3-C10 aryl, CN, each W is independently selected from O, C(CN)$_2$, C(CN)COOR' where R' is selected from C1-C10 alkyl, C1-C10 aryl and C1-C8 heteroaryl, and n is 0 or 1.

In one embodiment of the invention, R9 and R10 form a ring, preferably a 5-membered or 6-membered ring.

Compounds preferred in the context of the formula I are present when

U is N—R7 where R7 is selected from straight-chain or branched, substituted or unsubstituted alkyl or cycloalkyl having 1 to 10 carbon atoms or substituted or unsubstituted aryl or heteroaryl having 3-10 atoms, R1 to R6 are each H, Y is C—R9 where R9 is selected from H, halogen, C1-C30 alkyl, C1-C30 alkenyl, C1-C30 alkynyl, each linear or branched, substituted or unsubstituted, OR', SR', SiR'$_3$, NR'$_2$, where R' is selected from C1-C10 alkyl, C1-C10 aryl and C1-C8 heteroaryl, Z or C—R10 is with R10 selected from H, halogen, C1-C30 alkyl, C1-C30 alkenyl, C1-C30 alkynyl, each linear or branched, substituted or unsubstituted, OR', SR', SiR'$_3$, NR'$_2$, where R' is selected from C1-C10 alkyl, C1-C10 aryl and C1-C8 heteroaryl, X is S and W is C(CN)$_2$.

Compounds preferred in the context of formula II are present when n is 0 or 1,

U is N—R7 or CR7R8, where R7 and R8 are each independently selected from straight-chain or branched, substituted or unsubstituted alkyl or cycloalkyl having 1 to 10 carbon atoms and substituted or unsubstituted aryl or heteroaryl having 3-10 atoms, Y or C—R9 is with R9 selected from H, halogen, C1-C30 alkyl, C1-C30 alkenyl, C1-C30 alkynl, each linear or branched, substituted or unsubstituted, OR', SR', SiR'$_3$, NR'$_2$, where R' is selected from C1-C10 alkyl, C1-C10 aryl and C1-C8 heteroaryl, Z or C—R10 is with R10 selected from H, halogen, C1-C30 alkyl, C1-C30 alkenyl, C1-C30 alkynl, each linear or branched, substituted or unsubstituted, OR', SR', SiR'$_3$, NR'$_2$, where R' is selected from C1-C10 alkyl, C1-C10 aryl and C1-C8 heteroaryl, W is C(CN)$_2$ and R1 to R6 are each H.

Specific examples include the following compounds of the general formula I a to k:

| No. | U | R7 | R8 | R2/R3 | Y | Z | R1/R6 | W | X |
|---|---|---|---|---|---|---|---|---|---|
| a | NR7 | Propyl | — | H | C-butyl | CH | H | C(CN)2 | S |
| b | NR7 | Propyl | — | H | C-butyl | CH | H | O | S |
| c | NR7 | Phenyl | — | H | C-butyl | CH | H | C(CN)2 | S |
| d | NR7 | Phenyl | — | H | C-butyl | CH | H | O | S |
| e | NR7 | Methyl | — | H | CH | CH | H | C(CN)2 | S |
| f | NR7 | Propyl | — | H | CH | CH | H | C(CN)2 | O |
| g | NR7 | Hexyl | — | H | CH | CH | H | C(CN)2 | S |
| h | SiR7R8 | Propyl | Propyl | H | C-butyl | CH | H | C(CN)2 | S |
| i | SiR7R8 | Propyl | Propyl | H | C-butyl | CH | H | O | S |
| j | CR7R8 | Propyl | Propyl | H | C-propyl | C-propyl | H | C(CN)2 | S |
| k | CR7R8 | Propyl | Propyl | H | C-propyl | C-propyl | H | O | S |

Specific examples include the following compounds of the general formula II a to f:

| No. | U1/U2 | R7 | R8 | R2-R5 | Y | Z | R1/R6 | W | X | n |
|---|---|---|---|---|---|---|---|---|---|---|
| a | NR7 | Propyl | — | H | — | — | H | C(CN)2 | — | 0 |
| b | NR7 | Propyl | — | H | — | — | H | O | — | 0 |
| c | NR7 | Propyl | — | H | C-propyl | C-propyl | H | C(CN)2 | S | 1 |
| d | NR7 | Propyl | — | H | C-propyl | C-propyl | H | O | S | 1 |
| e | CR7R8 | Propyl | Propyl | H | — | — | H | C(CN)2 | — | 0 |
| f | CR7R8 | Propyl | Propyl | H | — | — | H | O | — | 0 |

The preparation of the inventive compounds can be achieved via various reaction steps known to those skilled in the art. The central unit where U, U1 or U2=NR can be prepared, for example, according to Zotti (Zotti et al., Makromol. Chem. 1992, 193, 399).

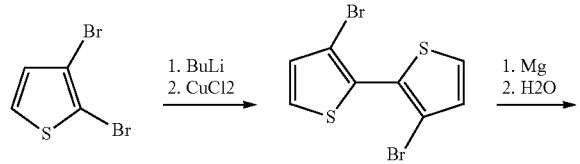

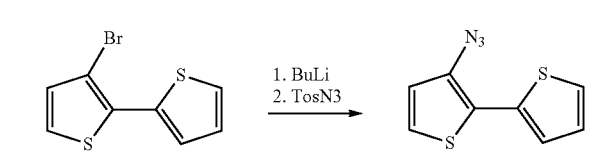

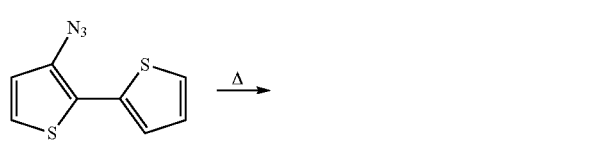

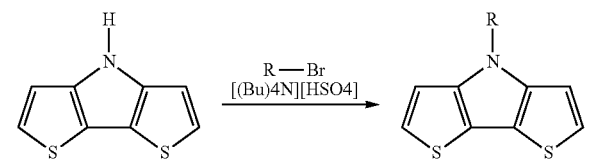

or according to Rasmussen (Rasmussen et al., Org. Chem. 2001, 66, 9067)

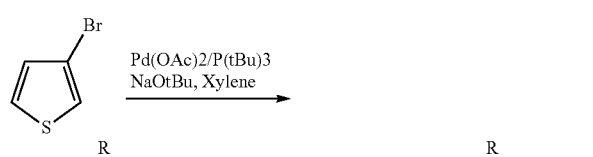

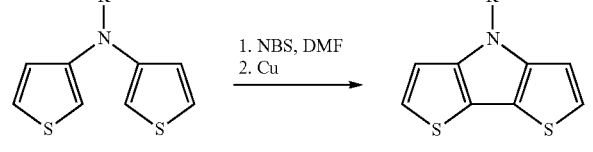

or according to Barlow (Barlow et al., Chem. Eur. J. 2007, 13, 9637)

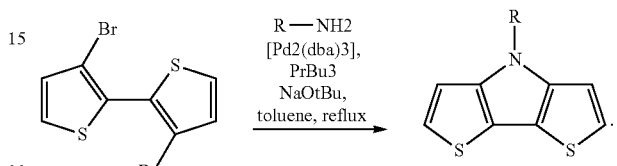

A central unit where U, U1 or U2=CR$_2$ can be prepared, for example, according to Jacek Z. Brzezinski, John R. Reynolds, Synthesis 2002 (8) 1053-1056:

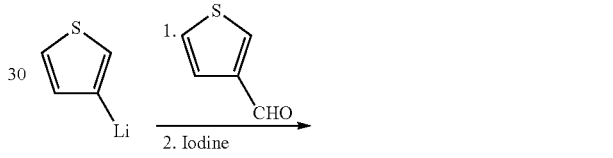

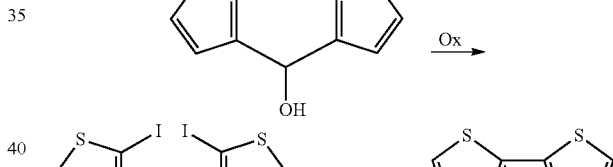

A central unit where U, U1 or U2=SiR2 can be prepared, for example, according to Hakan Usta, Gang Lu, Antonio Facchetti, Tobin J. Marks, J. Am. Chem. Soc. 2006 (128) 9034-9035:

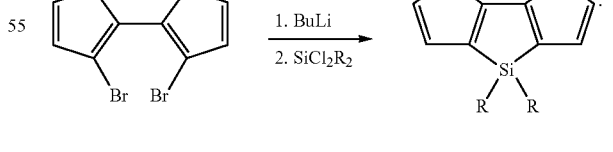

The further heterocyclic 5-membered rings are coupled via one of the customary methods for unsymmetric linkage of two (hetero)aromatics (e.g. Negishi, Stille, Suzuki, Kumada etc.) and is known to those skilled in the art (Rasmussen et al., Org. Lett. 2005, 7, 23, 5253, McCullough et al., Adv. Func. Mat. 2009, 19, 3427, Gronowitz, Hörnfeldt, "Thiophenes", Elsevier 2004):

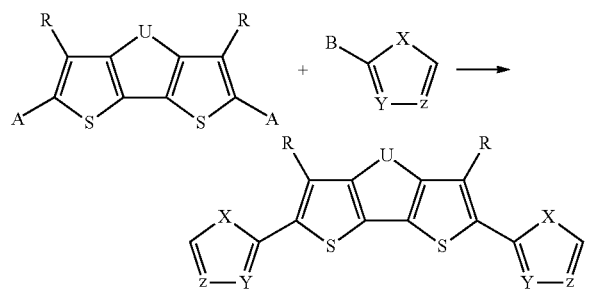

In this scheme, A and B are each metal or halogen components.

The coupling of two central units to give a compound of the general formula II where n=0 can take place unsymmetrically by the methods described above, where A'=B:

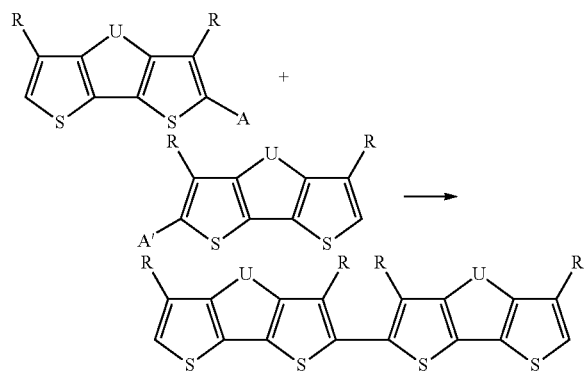

In addition, symmetric homolytic coupling is possible in the case that A'=A=halogen, for example by reaction with magnesium followed by copper chloride or BuLi followed by copper chloride (general description in Gronowitz, Hörnfeldt, "Thiophenes", Elsevier 2004).

The formation of compounds of the general formula II where n=1 is possible, for example, by the coupling methods already mentioned:

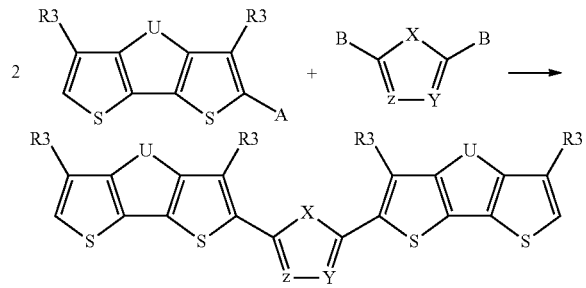

A and B are each metal or halogen components.

The terminal acceptor groups can be introduced, for example, by methods known to those skilled in the art, for example Gattermann, Gattermann-Koch, Houben-Hoesch, Vilsmeier/Vilsmeier-Haack, Friedel-Crafts acylation (general description in Organikum, Wiley-VCH), or after lithiation by a reaction with an acid derivative or carbonylating reagent.

Further acceptor groups are achievable by transfunctionalization of the above-described carbonyl function C(O)R, for example by Knoevenagel condensation (general description in Organikum, Wiley-VCH).

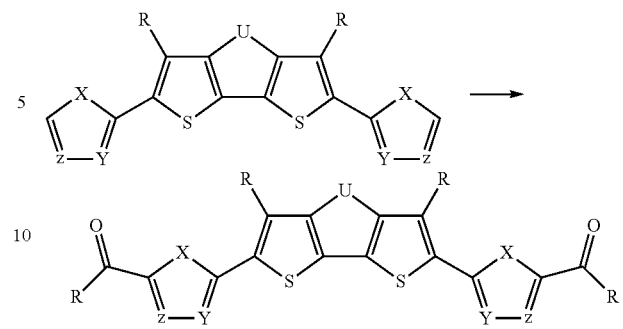

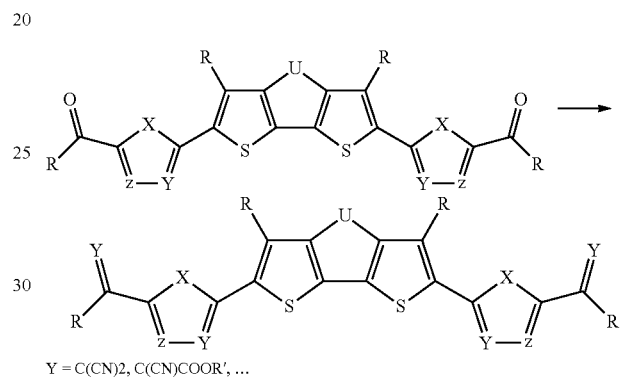

Y = C(CN)2, C(CN)COOR', ...

In the case that R1=R6=CN and W=C(CN)$_2$, the acceptor end groups can be introduced, for example, with BuLi and tetracyanoethylene (Cai et al., J. Phys. Chem. B 2006, 110, 14590):

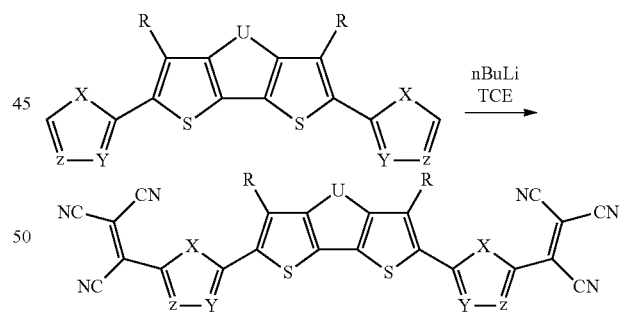

Alternatively, the reaction can also be performed without BuLi in DMF (Pappenfus et al., Org. Lett. 2008, 10, 8, 1553).

The sequence of the reactions can be varied.

In addition, the object is achieved by an optoelectronic component.

In one embodiment of the invention, an optoelectronic component having an electrode and a counterelectrode and at least one organic light-sensitive layer between the electrode (2) and the counterelectrode is specified, wherein the organic light-sensitive layer comprises at least one compound according to claim 1 and/or 2.

In a further embodiment of the invention, the optoelectronic component takes the form of an organic solar cell.

In a further embodiment of the invention, the component takes the form of an organic pin solar cell or organic pin tandem solar cell or pin multiple solar cell. A tandem solar cell refers to a solar cell which consists of a vertical stack of two solar cells connected in series. A multiple solar cell refers to a solar cell which consists of a vertical stack of a plurality of solar cells connected in series, with a maximum of 10 solar cells connected in one stack.

In a further embodiment of the invention, one or more undoped, partly doped or fully doped transport layers are also present in the component. These transport layers preferably have a maximum absorption at <450 nm, more preferably <400 nm.

In a further embodiment of the invention, the layers of the layer system of the component take the form of a light trap which extends the optical pathway of the incident light.

In a further embodiment of the invention, at least one of the photoactive mixed layers comprises, as an acceptor, a material from the group of the fullerenes or fullerene derivatives ($C_{60}$, $C_{70}$, etc.).

In a further embodiment of the invention, the contacts consist of metal, a conductive oxide, especially ITO, ZnO:Al or other TCOs, or a conductive polymer, especially PEDOT:PSS or PANI.

In a further embodiment, a p-doped layer is also present between the first electron-conductive layer (n layer) and the electrode present on the substrate, such that the structure is a pnip or pni structure, with the doping preferably selected at such a level that the direct pn contact does not have any barrier effect, but results in low-loss recombination, preferably as a result of a tunneling process.

In a further embodiment of the above-described structures, these take the form of an organic tandem solar cell or multiple solar cell. For instance, the component may be a tandem cell composed of a combination of nip, ni, ip, pnip, pni, pip, nipn, nin, ipn, pnipn, pnin or pipn structures, in which multiple independent combinations containing at least one i layer are stacked one on top of another (cross-combinations).

In a further embodiment of the above-described structures, this takes the form of a pnipnipn tandem cell.

In one embodiment of the invention, the component is formed with at least one inorganic layer comprising one or more inorganic materials.

In a further embodiment of the invention, the component is used on flat, curved or flexible carrier surfaces. These carrier surfaces are preferably plastic films or metal foils (e.g. aluminum, steel), etc.

Figure 2:
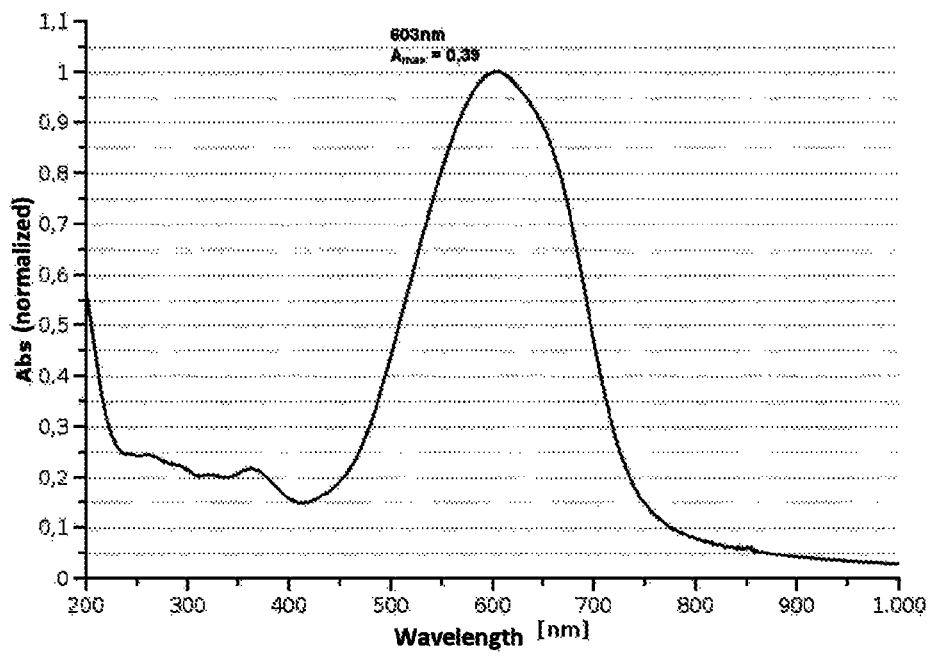
Figure 3:
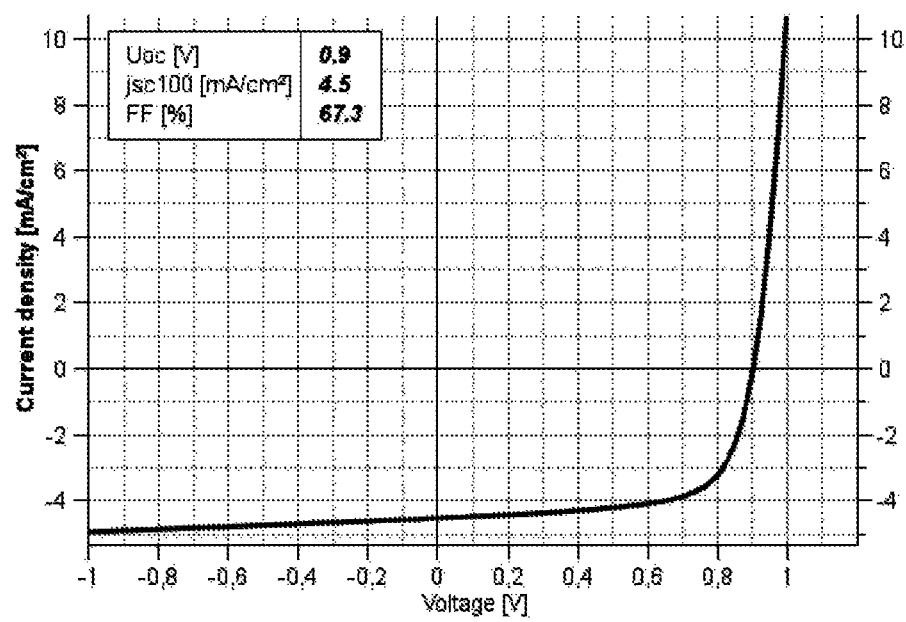
Figure 4:
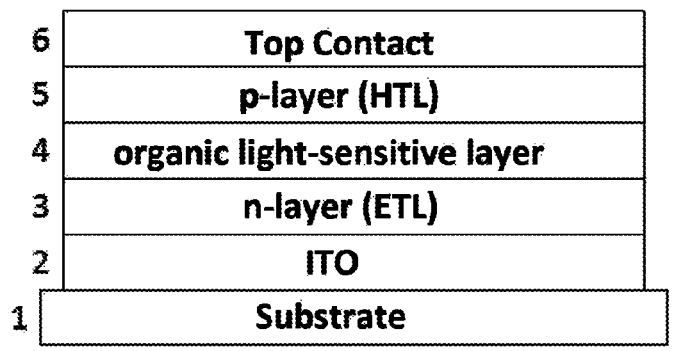

The invention is to be illustrated in detail hereinafter by some working examples and corresponding figures. The figures show:

FIG. 1 a reaction scheme for preparation of the compounds Ic and Id,

FIG. 2 a schematic representation of an absorption spectrum of compound Ic,

FIG. 3 a schematic diagram of a current-voltage curve of an Mip cell with a mixed layer of compound Ic, and FIG. 4 the schematic diagram of a structure of an illustrative photoactive component.

FIGS. 5A to 9B show the absorption spectra of further inventive compounds and the current-voltage curve of the corresponding Mip cells with these compounds.

The working examples adduced illustrate some inventive components by way of example. Parameters important for characterization are the fill factor, open-circuit voltage and short-circuit current listed, which are inferred from the current-voltage characteristic. The working examples are intended to describe the invention without restricting it thereto.

WORKING EXAMPLE 1

In a first working example, FIG. 1 shows a schematic of the preparation of compounds Ic and Id.

The individual preparation steps are specified hereinafter:
Preparation of Compound B:

An autoclave is initially charged with (A) (4.125 g, 12.75 mmol), t-BuONa (2.95 g, 30.7 mmol), $Pd_2dba_3$ (293 mg, 0.32 mmol), 2,2'-bis(diphenylphosphino)-1,1'-binaphthyl (793 mg, 1.27 mmol), 25 ml of toluene are added and the reaction mixture is blanketed with argon. Phenylamine (752.5 mg, 12.725 mmol) is added, and the mixture is heated (110° C.) for 12 hours. After cooling, 40 ml of water are added. The organic phase is removed, and the aqueous phase is extracted with $Et_2O$. The combined organic phases are dried over $Na_2SO_4$ and concentrated. The residue is purified by chromatography (silica gel, PE $CH_2Cl_2$ 10-1). Yield: 2.59 g (92%) of (B). 1H NMR: ($CDCl_3$) 7.16 (d, 2H), 7.03 (d, 2H), 4.04 (t, 2H), 1.93 (m, 2H), 0.97 (t, 3H)

Preparation of Compound C

In an Ar-blanketed 250 ml 3-neck round-bottom flask, (B) (1 g, 4.5 mmol) is dissolved in 100 ml of THF (abs.) and cooled to −78° C. nBuLi (2.5 M in hexane, 4.5 ml, 11.3 mmol) is added dropwise, and the reaction mixture is kept at −78° C. for approx. 1 hour and then gradually warmed to RT for 1 h, then cooled again to −78° C. Me3SnCl (1.0 M in hexane, 11.3 ml, 11.3 mmol) is added and, after approx. 1 hour, the reaction mixture is thawed. After 2 hours, water (100 ml) is added, and the aqueous phase is extracted with 50 ml of Et20. The combined organic phases are dried and concentrated. Yield 2.37 g (96%) of (C). 1H NMR: (CDCl3) 6.97 (s, 2H), 4.12 (m, 2H), 1.89 (m, 2H), 0.93 (m, 3H), 0.36 (s, 9H)

Preparation of Compound D

A reaction vessel is initially charged under argon with (C) (2.37 g, 4.3 mmol), 2-bromo-3-butylthiophene (2.3 g, 10.49 mmol) and 250 mg of Pd[PPh3]4, 30 ml of toluene are added and the mixture is heated under reflux for 48 hours. The reaction mixture is washed with NH4Cl (sat.) and water, and concentrated. The residue is purified by chromatography (silica gel, PE $CH_2Cl2$ 10-1). Yield: 1.217 g (57%) of (D). 1H NMR: ($CDCl_3$) 7.21 (d, 2H), 7.04 (s, 2H), 6.97 (d, 2H), 4.20 (t, 2H), 2.85 (t, 4H), 1.96 (m, 2H), 1.67 (m, 4H), 1.44 (m, 4H), 0.98 (m, 6H), 0.88 (3H).

Preparation of Compound Id

In a 100 ml one-neck round-bottom flask, DMF (2.27 ml, 29.3 mmol) and POCl3 (2.46 ml, 26.4 mmol) are dissolved in 30 ml of CH2Cl2 and the mixture is stirred at RT for 2 hours. Thereafter, (D) (1.217 g, 2.44 mmol) in 50 ml of $CH_2Cl_2$ is added dropwise and the mixture is stirred at RT for 48 hours. 50 ml of NaHCO3 (sat.) solution are added to the reaction mixture which is stirred at RT for 2 hours. The organic phase is removed and twice washed with 50 ml of water and dried. The solvent is distilled off, and the residue is purified by chromatography (silica gel, CH2Cl2-MeOH 500-3). Yield: 827 mg (62%) of (Ib). 1H NMR: (CDCl3), 9.85 (s, 2H), 7.63 (s, 2H), 7.23 (s, 2H), 4.25 (t, 2H), 2.91 (t, 4H), 1.98 (m, 2H), 1.72 (m, 4H), 1.49 (m, 4H), 0.98 (m, 9H)

Preparation of Compound Ic

In a 250 ml one-neck round-bottom flask, (1d) (723 mg, 1.3 mmol) and malononitrile (862 mg, 13 mmol) are dissolved in 150 ml of 1,2-DCE, and piperidine (11 mg, 0.13 mmol) is added. After heating under reflux for 48 h, the solvent is removed and the solids are digested with water under reflux for 2 h. The precipitate is removed, washed repeatedly with water and then with MeOH, and dried. The residue is purified by chromatography (silica gel, $CH_2Cl_2$). Yield: 370 mg (45%) of (Ic). 1H NMR: (C2D2Cl4, 373 K), 7.73 (s, 2H), 7.63 (s, 2H), 7.36 (s, 2H), 4.27 (t, 2H), 2.96 (t, 4H), 2.05 (m, 2H), 1.79 (m, 4H), 1.53 (m, 4H), 1.07 (m, 9H)

By vacuum sublimation at 10-6 to 10-8 mbar, a layer of thickness 30 nm was produced, determined by means of an oscillating crystal monitor. Compound Ic can be sublimed under reduced pressure with good yield. The absorption maximum is, as shown in FIG. 2, at 603 nm with an absorption of 0.39.

In a further working example, an MIP component consisting of a sample on glass with a transparent ITO top contact, a layer of Buckminster fullerene $C_{60}$, a 2:1 mixed layer of compound Ic with $C_{60}$, a p-doped hole transport layer and a gold layer are produced. FIG. 3 shows the current-voltage curve of this MIP cell with a mixed layer of compound Ic with C60.

The most important parameters, such as the fill factor FF, the open-circuit voltage $U_{oc}$ and the short circuit current $j_{sc}$ show a well-functioning organic solar cell.

The following compounds have to date been prepared in a similar manner:

| No. | 1H NMR | UV: λmax (film) |
|---|---|---|
| Ia | (C2D2Cl4, 373 K) 7.73 (s, 2H), 7.63 (s, 2H), 7.36 (s, 2H), 4.27 (t, 2H), 2.96 (t, 4H), 2.05 (m, 2H), 1.79 (m, 4H), 1.53 (m, 4H), 1.07 (m, 9H) | 627 nm |
| Ib | (CDCl3) 9.85 (s, 2H), 7.63 (s, 2H), 7.23 (s, 2H), 4.25 (t, 2H), 2.91(t, 4H), 1.98(m, 2H), 1.72 (m, 4H), 1.49 (m, 4H), 0.98 (m, 9H) | |
| Ic | (C2D2Cl4, 373 K) 9.78 (s, 2H), 7.61 (s, 2H), 7.04 (s, 2H), 4.14 (t, 4H), 2.71 (t, 4H), 1.87 (m, 4H), 1.57 (m, 4H), 1.01 (t, 6H), 0.92 (t, 6H) | 603 nm |
| Id | (CDCl3) 9.85 (s, 2H), 7.63 (m, 7H), 7.37 (s, 2H), 2.91 (t, 4H), 1.73 (m, 4H), 1.46 (m, 4H), 1.00 (t, 6H) | |
| Ie | In TCE-d2 at 100° C., ppm: 7.78 (s, 2H), 7.71 (d, 2H), 7.42 (s, 2H), 7.39(d, 2H), 3.98 (s, 3H) | 638 nm |
| If | In TCE-d2 at 100° C., ppm: 7.58 (s, 2H), 7.42 (s, 2H), 7.36 (d, 2H), 6.89 (d, 2H), 4.29 (t, 2H), 2.05 (qa, 2H), 1.07 (t, 3H) | 600 nm |
| Ig | In TCE-d2 at 100° C., ppm: 7.77 (s, 2H), 7.71 (d, 2H), 7.40 (s, 2H), 7.39 (d, 2H), 4.28 (t, 3H), 2.00 (m, 2H), 1.43 (m, 6H), 0.97 (t, 3H) | 637 nm |
| Ih | 1H NMR (CDCl3, 293 K): 0.98 ppm (m, 16H), 1.45 (m, 8H), 1.69 (m, 4H), 2.85 (m, 4H), 7.40 (s, 2H), 7.52 (s, 2H), 7.70 (s, 2H) | 598 nm |
| Ii | 1H NMR (CDCl3, 293 K): 0.98 ppm (m, 16H), 1.46 (m, 8H), 1.70 (m, 4H), 2.84 (m, 4H), 7.28 (s, 2H), 7.60 (s, 2H), 9.83 (s, 2H) | |
| Ij | 1H NMR (CDCl3, 293 K): 0.81 ppm (t, 6H), 0.98 (m, 4H), 1.05 (t, 6H), 1.10 (t, 6H), 1.58 (m, 4H), 1.61 (m, 4H), 1.93 (m, 4H), 2.70 (m, 4H), 2.80 (m, 4H), 7.30 (s, 2H), 7.81 (s, 2H) | 586 nm |
| Ik | 1H NMR (CDCl3, 293 K): 0.80 ppm (t, 6H), 1.05 (m, 10H), 1.07 (t, 6H), 1.63 (m, 4H), 1.68 (m, 4H), 1.87 (m, 4H), 2.75 (m, 4H), 2.89 (m, 4H), 7.17 (s, 2H), 10.00 (s, 2H) | |
| IIa | Insoluble | 616 nm |
| IIb | (C2D2Cl4, 373 K) 9.68 (s, 2H), 7.69 (s, 2H), 7.22 (s, 2H), 4.23 (t, 4H), 1.97 (m, 4H), 1.02 (t, 6H) | |
| IIc | (C2D2Cl4, 373 K) 7.77 (s, 2H), 7.74 (s, 2H), 7.17 (s, 2H), 4.28 (t, 4H), 2.90 (t, 4H), 2.06 (m, 4H), 1.76 (m, 4H), 1.15 (t,6H), 1.08 (t, 6H) | 597 nm |
| IId | (C2D2Cl4, 373 K) 9.78 (s, 2H), 7.61 (s, 2H), 7.04 (s, 2H), 4.14 (t, 4H), 2.71 (t, 4H), 1.87 (m, 4H), 1.57 (m, 4H), 1.01 (t, 6H), 0.92 (t, 6H) | |
| IIe | 1H NMR (CDCl3, 293 K): 0.81 ppm (t, 12H), 0.99 (m, 8H), 1.91 (m, 8H), 7.16 (s, 2H),7.53 (s, 2H), 7.73 (s, 2H) | 601 nm |
| IIf | 1H NMR (CDCl3, 293 K): 0.80 ppm (t, 12H), 1.01 (m, 8H), 1.88 (m, 8H), 7.12 (s, 2H), 7.57 (s, 2H), 9.83 (s, 2H) | |

WORKING EXAMPLE 2

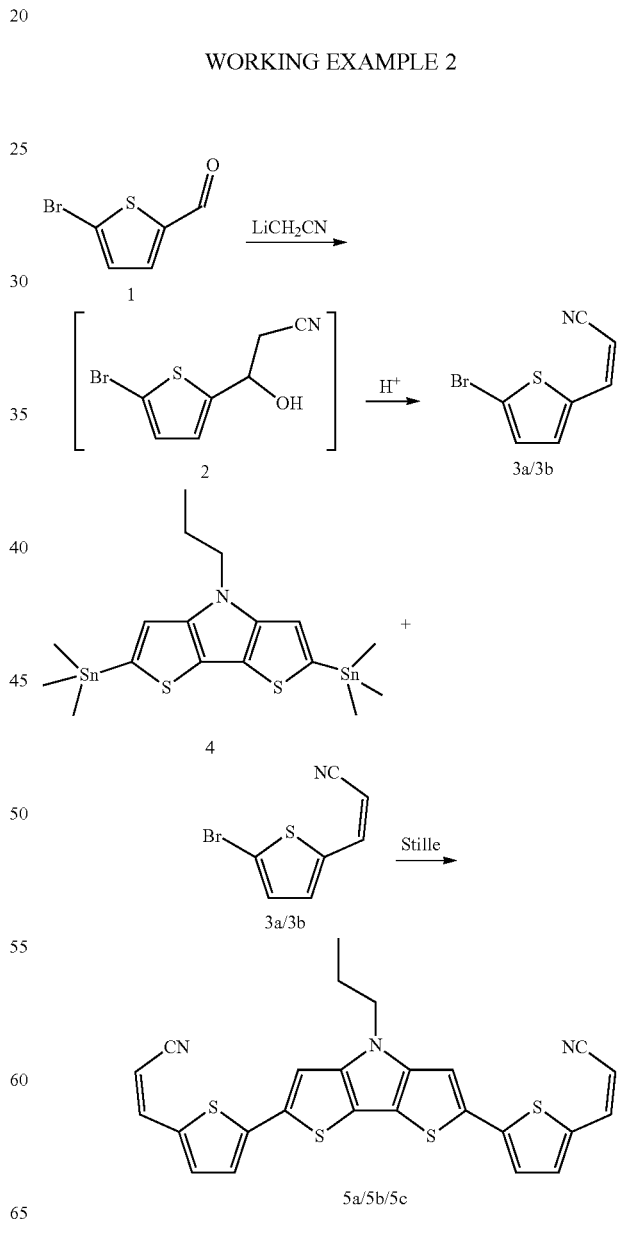

General Method for Stille Coupling (GM1)

The bis-stannyl compound and 3 equivalents of the bromo compound are dissolved in dry THF. Pd(PPh$_3$)$_4$ is added and the reaction mixture is heated to reflux temperature. After cooling to room temperature, the mixture is filtered and the residue is washed with THF and methanol. The crude product is purified either by means of chromatography or by recrystallization, in order to isolate the product in clean form.

General Method for Knoevenagel Reaction (GM2)

The aldehyde and malonitrile are dissolved in ethanol, piperidine is added thereto and the mixture is heated under reflux for 2 h. After cooling, the precipitate is filtered off and washed with ethanol and hexane. The crude product is recrystallized in order to isolate the product in clean form.

4-Propyl-2,6-bistrimethylstannyl-4H-dithieno[3,2-b; 2',3'-d]pyrrole (4)

To a solution of 1.1 g (5.0 mmol) of 4-propyl-4H-dithieno [3,2-b;2',3'-d]pyrrole (32) in 17 ml of dry THF are added 6.9 ml (11.0 mmol) of a 1.6 M n-butyllithium/hexane solution at −78° C. After the mixture has been stirred at −78° C. for 1 h, the cooling bath is removed and the mixture is stirred at room temperature for a further hour. A precipitate forms during this time. The suspension is cooled −78° C. and a solution of 2.2 g (11.0 mmol) of trimethylstannyl chloride dissolved in 3 ml of THF is added. The mixture is stirred −78° C. for 1 h and then the cooling bath is removed to stir at room temperature for a further 3 h. 50 ml of n-hexane are added and hydrolysis is effected with water. The organic phase is washed three times with 50 ml of water and dried over sodium sulfate. After the solvents have been distilled off, the residue is dried under reduced pressure and the crude product (2.26 g, 88%) is used in the next stage without further purification. 1H NMR (CDCl$_3$): 7.01 ppm (s, 2H), 4.16 (t, 2H), 1.94 (qa, 2H), 0.98 (t, 3H), 0.40 (s, 18H).

3-(5-Bromo-2-thienyl)prop-2-enenitrile (3a/b)[1]

To a solution of 6.0 ml (10.8 mmol) of 1.8 M LDA-THF solution in 10 ml of THF is added dropwise 0.56 ml (10.8 mmol) of acetonitrile at −78° C. The mixture is stirred for 30 min. 1.91 g (10.0 mmol) of 5-bromothiophene-2-carbaldehyde (1) are added thereto and the mixture is stirred at −78° C. for 1 h. The reaction mixture is warmed to −20° C. and saturated NH$_4$Cl solution (2 ml) is added. The phases are separated and the aqueous phase is extracted with ether (30 ml). The combined organic phases are dried over sodium sulfate. The solvents are distilled off to obtain a brown oil. The brown oil is dissolved in 5 ml of acetic anhydride and 0.1 ml of conc. phosphoric acid. This reaction mixture is heated to 100° C. for 2 h. 30 ml of water are added and the aqueous phase is extracted with 50 ml of ether. The organic phase is washed to neutrality with portions of sodium hydrogencarbonate solution and dried over sodium sulfate. After the solvents have been distilled off, the residue is purified by means of chromatography (SiO$_2$, DCM:hexane (1:1)). This gives 0.78 g (36%) of product as E/Z isomers. 1H NMR (CDCl$_3$) E isomer: 7.25 ppm (d, 1H), 7.11 (d, 1H), 7.08 (d, 1H), 5.26 (d, 1H). Z isomer: 7.33 (d, 1H), 7.04 (d, 1H), 6.98 (d, 1H), 5.54 (d, 1H).

3-(5-{6-[5-(2-Cyanovinyl)thiophen-2-yl]-4-propyl-4H-dithieno[3,2-b;2',3'-d]pyrrol-2-yl}thiophen-2-yl) prop-2-enenitrile (5a/b/c)

According to GM1,3-(5-bromo-2-thienyl)prop-2-enenitrile (3a/b) (578 mg, 2.70 mmol) and 4-propyl-2,6-bistrimethylstannyl-4H-dithieno[3,2-b;2,3'-d]pyrrole (4) (490 mg, 0.90 mmol) are dissolved in 5 ml of THF, Pd(PPh$_3$)$_4$ (104 mg, 0.09 mmol) is added and the mixture is heated to 70° C. for 16 h. After workup, the crude product is purified by means of chromatography (SiO$_2$, DCM). This gives three products (60 mg (14%) of Z,Z isomer, 60 mg (14%) of E,E isomer and 100 mg (23%) of E,Z isomer) in a total yield of 50%.

1H NMR (TCE-d2, 375 K) Z,Z isomer: 7.36 ppm (d, 2H), 7.18 (s, 2H), 7.14 (d, 2H), 7.11 (d, 2H), 5.16 (d, 2H), 4.12 (dd, 2H), 1.93 (qa, 2H), 0.98 (t, 3H). UV (film): 500 nm. E,E isomer: 7.35 (d, 2H), 7.11 (s, 2H), 7.10 (d, 4H), 5.54 (d, 2H), 4.11 (dd, 2H), 2.92 (qa, 2H), 0.97 (t, 3H). UV (film): 521 nm. E, Z isomer: 7.35 (m, 2H), 7.18 (s, 1H), 7.11 (m, 5H), 5.53 (d, 1H), 5.17 (d, 1H), 4.11 (dd, 2H), 1.92 (qa, 2H), 0.98 (t, 3H). UV (film): 514 nm.

WORKING EXAMPLE 3

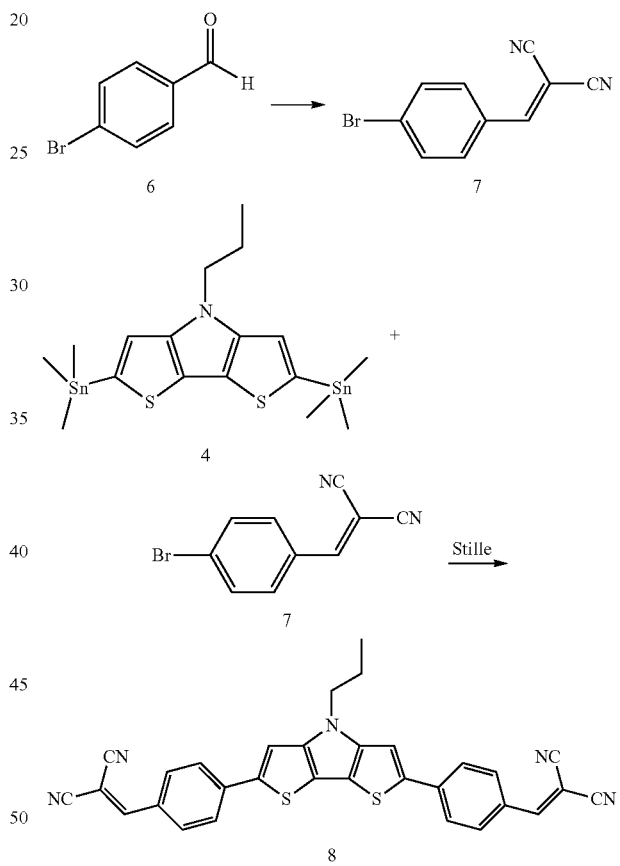

2-[(4-Bromophenyl)methylene]propanedinitrile (7)

According to GM2,4-bromobenzaldehyde (6) (1.0 g, 5.40 mmol) and malonitrile (429 mg, 6.48 mmol) are dissolved in 15 ml of ethanol, piperidine (50 µl, 0.05 mmol) is added, and the mixture is heated for 2 h. After workup, the crude product is recrystallized from ethanol to obtain 775 mg (62%) of product. 1H NMR (CDCl$_3$): 7.77 ppm (d, 2H), 7.72 (s, 1H), 7.69 (d, 2H).

Dicyanovinyl Compound 8

According to GM1, 2-[(4-bromophenyl)methylene]propanedinitrile (7) (699 mg, 3.00 mmol) and 4-propyl-2,6-bistrimethylstannyl-4H-dithieno[3,2-b;2',3'-d]pyrrole (4) (547 mg, 1.00 mmol) are dissolved in 3.8 ml of THF, Pd(PPh$_3$)$_4$ (59 mg, 0.05 mmol) is added and the mixture is heated to 70° C. for 36 h. After workup, the crude product is recrystallized from chlorobenzene to obtain 120 mg (23%) of product. 1H NMR (TCE-d2, 375 K): 7.98 ppm (d, 4H), 7.85 (d, 4H), 7.76 (s, 2H), 7.49 (s, 2H), 4.29 (dd, 2H), 2.07 (qa, 2H), 1.11 (t, 3H). UV (film): 526 nm.

WORKING EXAMPLE 4

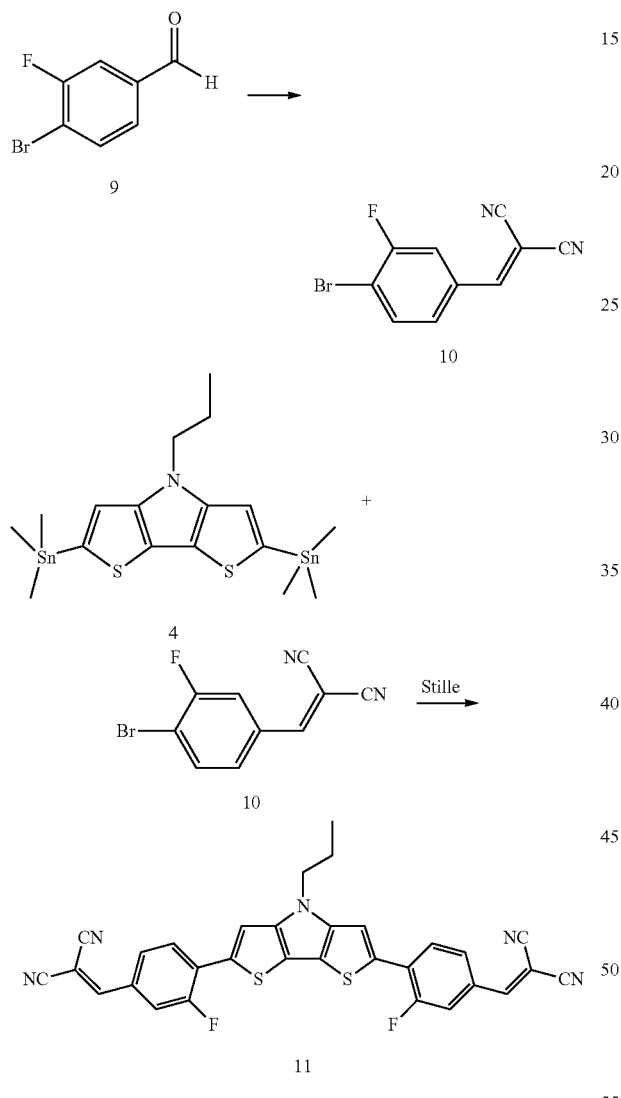

2-[(4-Bromo-3-fluorophenyl)methylene]propane-dinitrile (10)

According to GM2, 4-bromo-3-fluorobenzaldehyde (9) (820 mg, 4.04 mmol) and malonitrile (320 mg, 4.85 mmol) are dissolved in 15 ml of ethanol, piperidine (40 µl, 0.04 mmol) is added and the mixture is heated for 2 h. After workup, the crude product is recrystallized from ethanol to obtain 847 mg (84%) of product. 1H NMR (CDCl$_3$): 7.75 ppm (dd, 1H), 7.70 (s, 1H), 7.68 (dd, 1H), 7.56 (dd, 1H).

Dicyanovinyl Compound 11

According to GM1, 2-[(4-bromo-3-fluorophenyl)-methylene]propanedintrile (10) (840 mg, 3.35 mmol) and 4-propyl-2,6-bistrimethylstannyl-4H-dithieno[3,2-b;2',3'-d]pyrrole (4) (610 mg, 1.12 mmol) are dissolved in 4.5 ml of THF, Pd(PPh$_3$)$_4$ (127 mg, 0.11 mmol) is added, and the mixture is heated to 70° C. for 20 h. After workup, the crude product is recrystallized from chlorobenzene to obtain 20 mg (3%) of product. 1H NMR (TCE-d2, 375 K): 7.78 ppm (dd, 2H), 7.69 (d, 2H), 7.65 (d, 2H), 7.61 (s, 2H), 7.59 (s, 2H), 4.21 (dd, 2H), 1.96 (qa, 2H), 0.99 (t, 3H).

WORKING EXAMPLE 5

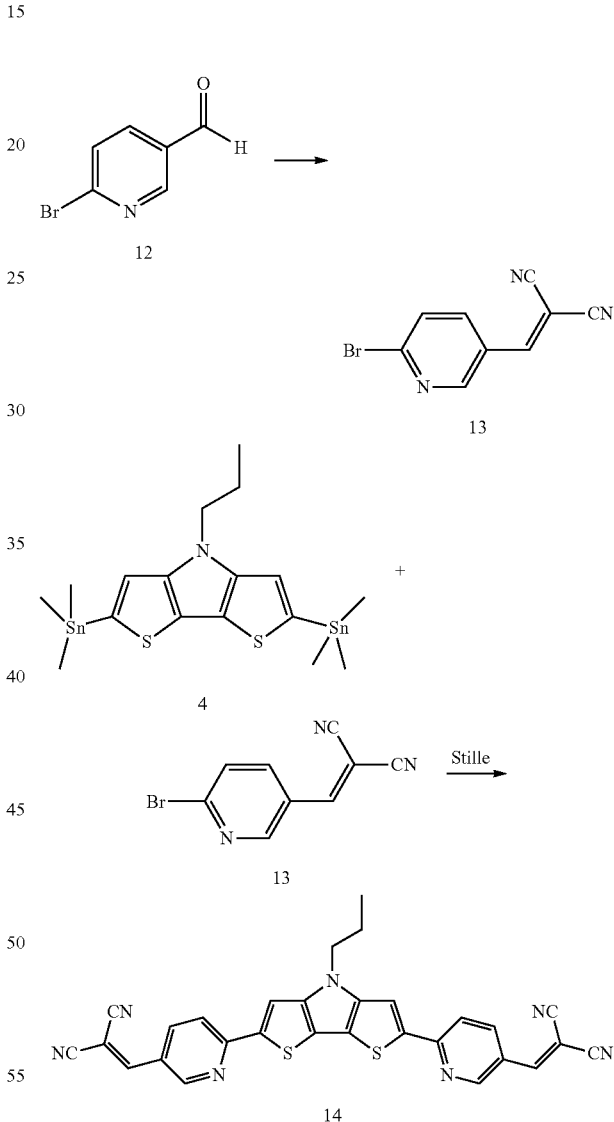

2-[(6-Bromo-3-pyridyl)methylene]propanedinitrile (13)

According to GM2, 6-bromopyridine-3-carbaldehyde (12) (1.0 g, 5.40 mmol); and malonitrile (429 mg, 6.48 mmol) are dissolved in 15 ml of ethanol, piperidine (50 µl, 0.05 mmol) is added, and the mixture is heated for 2 h. After workup, the crude product is recrystallized from ethanol to obtain 690 mg (55%) of product. 1H NMR (CDCl$_3$): 8.63 ppm, (d, 1H), 8.31 (dd, 1H), 7.76 (s, 1H), 7.71 (d, 1H).

Dicyanovinyl Compound 14

According to GM1, 2-[(6-bromo-3-pyridyl)methylene]-propanedintrile (13) (690 mg, 2.95 mmol) and 4-propyl-2,6-bistrimethylstannyl-4H-dithieno[3,2-b;2',3'-d]pyrrole (4) (547 mg, 1.00 mmol) are dissolved in 4.0 ml of THF, Pd(PPh$_3$)$_4$ (69 mg, 0.06 mmol) is added and the mixture is heated to 70° C. for 36 h. After workup, the crude product is recrystallized from chlorobenzene to obtain 320 mg (61%) of product. MALDI (m/z): 527.1. UV (film): 581 nm.

WORKING EXAMPLE 6

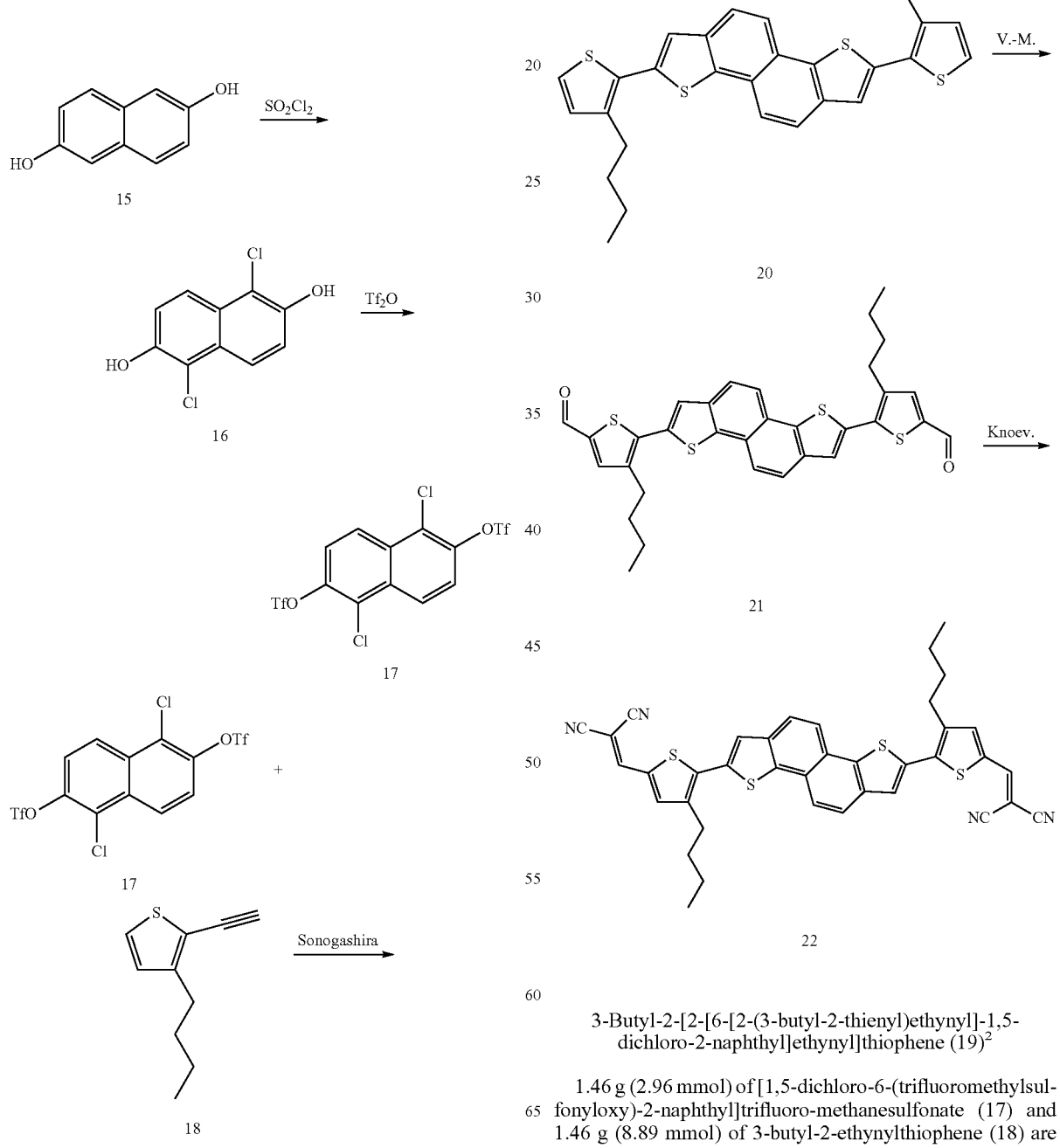

3-Butyl-2-[2-[6-[2-(3-butyl-2-thienyl)ethynyl]-1,5-dichloro-2-naphthyl]ethynyl]thiophene (19)[2]

1.46 g (2.96 mmol) of [1,5-dichloro-6-(trifluoromethylsulfonyloxy)-2-naphthyl]trifluoro-methanesulfonate (17) and 1.46 g (8.89 mmol) of 3-butyl-2-ethynylthiophene (18) are dissolved in 1.25 ml of dry triethylamine and 30 ml of dry THF. To the reaction mixture are added 208 mg (0.30 mmol) of Pd(PPh$_3$)$_2$Cl$_2$ and 113 mg (0.59 mmol) of copper(I) iodide. The mixture is heated under reflux for 20 h. 3 ml of water and 3 ml of 1N HCl solution are added thereto, the phases are separated and the aqueous phase is extracted three times with 25 ml of DCM. The combined organic phases are dried over sodium sulfate. After the solvents have been distilled off, the residue is recrystallized from hexane/chloroform to obtain 505 mg (33%) of product. 1H NMR (CDCl$_3$): 8.22 ppm (d, 2H), 7.68 (d, 2H), 7.27 (d, 2H), 6.94 (d, 2H), 2.88 (dd, 4H), 1.70 (m, 4H), 1.42 (qa, 4H), 0.96 (t, 6H).

2,7-bis(3-Butyl-2-thienyl)benzothiopheno[7,6-g]benzothiophene (20)

To a suspension of 932 mg (3.88 mmol) of sodium sulfide nonahydrate in 23 ml of NMP are added 505 mg (0.97 mmol) of naphthylethyne 19. The reaction mixture is heated under reflux for 16 h. After cooling to room temperature, 76 ml of ammonium chloride solution are added and extraction is effected three times with 30 ml of chloroform. The organics were combined and dried over anhydrous sodium sulfate. The combined organic phases are dried over sodium sulfate. After the solvents have been distilled off, the residue is purified by means of chromatography (SiO$_2$, n-hexane) to obtain 300 mg (60%) of product. 1H NMR (CDCl$_3$): 8.01 ppm (d, 2H), 7.88 (d, 2H), 7.47 (s, 2H), 7.27 (d, 2H), 7.01 (d, 2H), 2.91 (dd, 4H), 1.71 (m, 4H), 1.45 (qa, 4H), 0.96 (t, 6H).

4-Butyl-5-[2-(3-butyl-5-formyl-2-thienyl)benzothiopheno[7,6-g]benzothiophen-7-yl]thiophene-2-carbaldehyde (21)

To a solution of benzothiophenobenzothiophene 20 (300 mg, 0.58 mmol) in 7 ml of dichloromethane is added a solution of 1.1 ml (11.4 mmol) of phosphorus oxychloride and 0.94 ml (12.2 mmol) of DMF in 7 ml of DCM. The reaction mixture is refluxed for 16 h, then sat. sodium hydrogencarbonate solution (50 ml) is added and the mixture is stirred at room temperature for 2 h. After phase separation, the organic phase is dried over sodium sulfate. After the solvents have been distilled off, the residue is recrystallized from toluene to obtain 172 mg (52%) of product. 1H NMR (TCE-d2, 375 K): 9.83 ppm (s, 2H), 8.01 (d, 2H), 7.90 (s, 2H), 7.61 (s, 4H), 2.92 (dd, 4H), 1.72 (m, 4H), 1.44 (qa, 4H), 0.95 (t, 6H).

2-[[4-Butyl-5-[7-[3-butyl-5-(2,2-dicyanovinyl)-2-thienyl]benzothiopheno[7,6-g]benzothiopen-2-yl]-2-thienyl]methylene]propanedinitrile (22)

A solution of dialdehyde 21 (167 mg, 0.29 mmol), malonitrile (214 mg, 3.24 mmol) and piperidine (4 mg, 0.04 mmol) in 50 ml of 1,2-dichloroethane is refluxed for 48 h. After the solvent has been distilled off, the residue is suspended in water and refluxed for 2 h. The crude product is filtered, washed with water and methanol, and dried under reduced pressure. The residue is recrystallized from chlorobenzene to obtain 158 g (81%) of product. 1H NMR (TCE-d2, 375 K): 8.03 ppm (d, 2H), 7.92 (d, 2H), 7.69 (s, 2H), 7.68 (s, 2H), 7.61 (s, 2H), 2.94 (dd, 4H), 1.72 (m, 4H), 1.45 (qa, 4H), 0.96 (t, 6H).

WORKING EXAMPLE 7

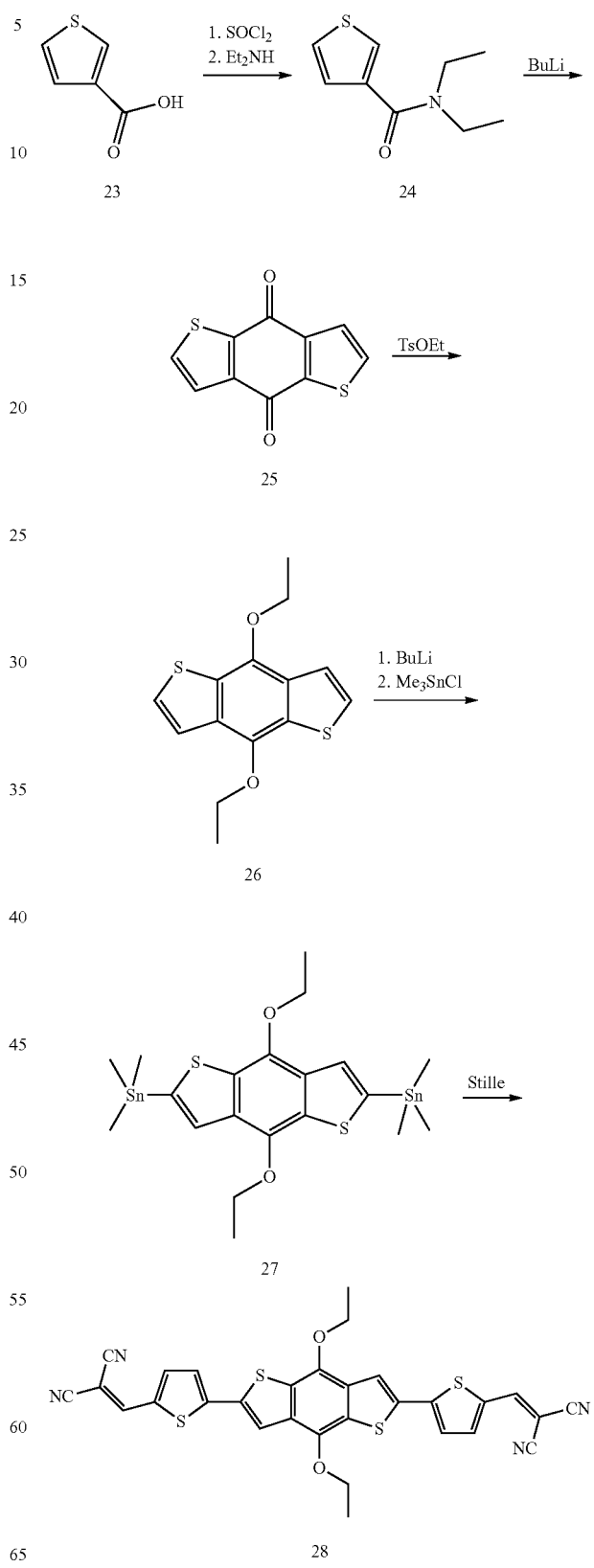

(4,8-Diethoxy-2-trimethylstannylthieno[2,3-f]benzothiophen-6-yl)trimethylstannane (27)[3]

To a solution of 556 mg (2.0 mmol) of 4,8-diethoxythieno[2,3-f]benzothiophene (26) in 8 ml of dry THF are added dropwise 1.6 ml (4.1 mmol) of 2.5 M n-butyllithium/hexane solution at −78° C. After the mixture has been stirred at −78° C. for 1 h, the cooling bath is removed and the mixture is stirred at room temperature for a further hour. The mixture is cooled to −78° C. and a solution of 4.2 ml (4.2 mmol) of 1.0 M trimethylstannyl chloride in n-hexane is added. The reaction mixture is stirred at −78° C. for another 10 min and then at room temperature for 16 h. 20 ml of ether and 20 ml of water are added and the organic phase is separated. The aqueous phase is extracted with 20 ml of ether, and the organic phases are combined and dried over sodium sulfate. After the solvents have been distilled off, the residue is dried under reduced pressure. The crude product (1.13 g, 94%) is used in the next stage without further purification. 1H NMR (CDCl$_3$): 7.51 ppm (s, 2H), 4.38 (qa, 4H), 1.50 (t, 6H), 0.45 (s, 18H).

Dicyanovinyl Compound 28

According to GM1, 2-[(5-bromo-2-thienyl)methylene]propanedinitrile (621 mg, 2.6 mmol) and (4,8-diethoxy-2-trimethylstannylthieno[2,3-f]benzothiophen-6-yl)trimethylstannane (27) (604 mg, 1.0 mmol) are dissolved in 4 ml of THF, Pd(PPh$_3$)$_4$ (59 mg, 0.05 mmol) is added and the mixture is heated to 70° C. for 16 h. After workup, the crude product is recrystallized from chlorobenzene to obtain 290 mg (49%) of product. 1H NMR (TCE-d2, 375 K): 7.84 ppm (s, 2H), 7.83 (s, 2H), 7.78 (d, 2H), 7.53 (d, 2H), 4.53 (qa, 4H), 1.62 (t, 6H). UV (film): 589 nm (max), 466 nm.

WORKING EXAMPLE 8

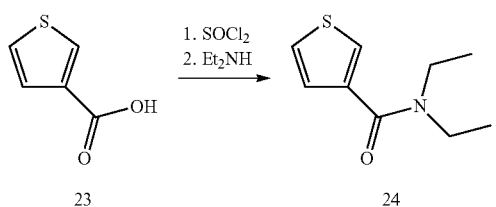

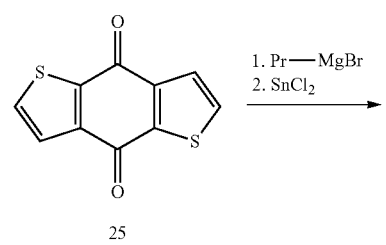

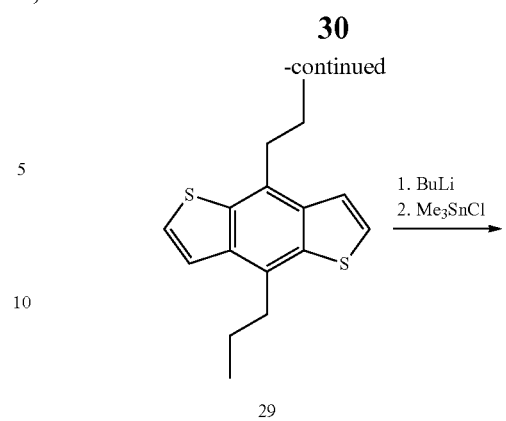

29

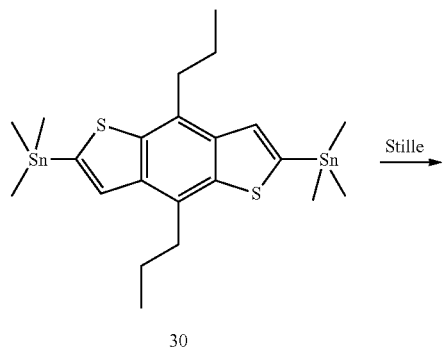

30

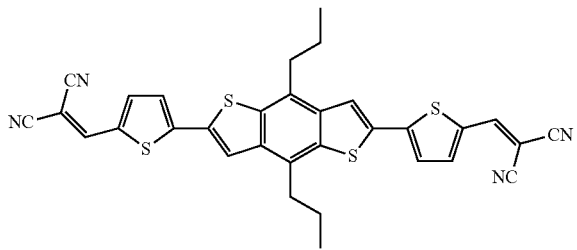

31

(4,8-Dipropyl-2-trimethylstannylthieno[2,3-f]benzothiophen-6-yl)trimethylstannane (30)[4]

To a solution of 400 mg (1.47 mmol) of 4,8-dipropylthieno[2,3-f]benzothiophene (29) in 6 ml of THF are added dropwise 1.2 ml (3.02 mmol) of 2.5 M n-butyllithium/hexane solution at −78° C. After the mixture has been stirred at −78° C. for 1 h, the cooling bath is removed and the mixture is stirred at room temperature for a further hour. The mixture is cooled to −78° C. and a solution of 3.2 ml (3.2 mmol) of 1.0 M trimethylstannyl chloride in n-hexane is added. The reaction mixture is stirred at −78° C. for another 10 min and then at room temperature for another 16 h. 20 ml of ether and 20 ml of water are added and the organic phase is separated. The aqueous phase is extracted with 20 ml of ether, and the organic phases are combined and dried over sodium sulfate.

After the solvents have been distilled off, the residue is dried under reduced pressure. The crude product (890 mg, 100%) is used in the next stage without further purification. 1H NMR (CDCl$_3$): 7.50 ppm (s, 2H), 3.21 (dd, 4H), 1.88 (qa, 4H), 1.07 (t, 6H), 0.45 (s, 18H).

Dicyanovinyl Compound 31

According to GM1, 2-[(5-bromo-2-thienyl)methylene]-propanedinitrile (538 mg, 2.25 mmol) and (4,8-diethoxy-2-trimethylstannylthieno[2,3-f]benzothiophen-6-yl)trimethylstannane (30) (450 mg, 0.75 mmol) are dissolved in 5 ml of THF, Pd(PPh$_3$)$_4$ (43 mg, 0.04 mmol) is added and the mixture is heated to 70° C. for 16 h. After workup, the crude product is recrystallized from chlorobenzene to obtain 301 mg (68%) of product. 1H NMR (TCE-d2, 375 K): 7.73 ppm (s, 2H), 7.72 (s, 2H), 7.67 (d, 2H), 7.44 (d, 2H), 3.14 (dd, 4H), 1.89 (qa, 4H), 1.07 (t, 6H). UV (film): 586 nm (max), 545 nm, 481 nm.

WORKING EXAMPLE 9

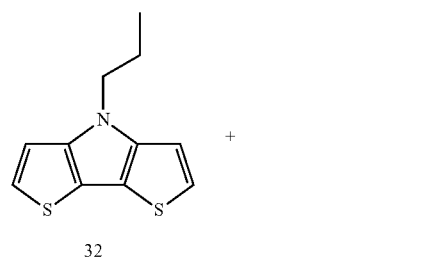

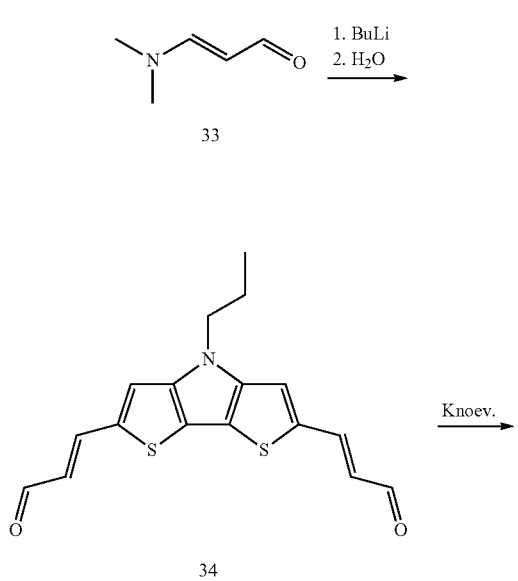

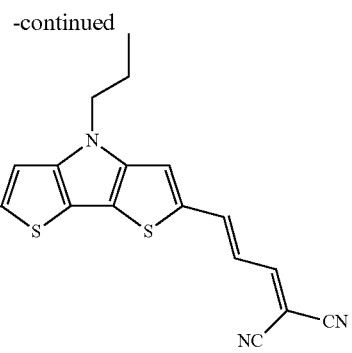

Diacroleindithienopyrrole 34[5]

To a solution of 490 mg (2.22 mmol) of 4-propyl-4H-dithieno[3,2-b;2',3'-d]pyrrole (32) in 9 ml of THF are added dropwise 1.9 ml (4.66 mmol) of 2.5 M n-butyllithium/hexane solution at −78° C. The mixture is stirred at −78° C. for 5 min, then stirred at −10° C. for 1 h. 770 mg (7.77 mmol) of 3-dimethylaminoacrolein (33) are added to the mixture which is stirred at −5° C. for 30 min. The cooling is removed and the mixture is stirred at room temperature for a further 4 h. 20 ml of sat. NH$_4$Cl solution are added and the reaction mixture is stirred for 1 h. 100 ml of DCM are added thereto, and the organic phase is separated and dried over sodium sulfate. After the solvents have been distilled off, the residue is purified by chromatography (SiO$_2$, DCM: ethyl acetate (10:1)) to obtain 152 mg (21%) of product. 1H NMR (CDCl$_3$): 9.64 ppm (d, 2H), 7.58 (d, 2H), 7.24 (s, 2H), 6.54 (dd, 2H), 5.14 (dd, 2H), 1.93 (qa, 2H), 0.97 (t, 3H).

Dicyanovinyl Compound 35

A solution of dialdehyde 34 (150 mg, 0.46 mmol), malonitrile (241 mg, 3.65 mmol) and piperidine (4 mg, 0.04 mmol) in 40 ml of 1,2-dichloroethane is refluxed for 5 days. After the solvent has been distilled off, the residue is suspended in water and refluxed for 2 h. The crude product is filtered, washed with water and methanol and dried under reduced pressure. The residue is recrystallized from chlorobenzene to obtain 77 mg (39%) of product. 1H NMR (TCE-d2, 375 K): 7.42 ppm (d, 2H), 7.32 (d, 2H), 7.23 (s, 2H), 7.01 (dd, 2H), 4.11 (dd, 2H), 1.90 (qa, 2H), 0.96 (t, 3H). UV (film): 611 nm (max), 663 nm.

LITERATURE

1. T. J. Dietsche, D. B. Gorman, J. A. Orvik, G. A. Roth, W. R. Shiang, *Organic Process Research & Development* 2000, 4, 4, 275-285.
2. S. Shinamura, E. Miyazaki, K. Takimiya, *J. Org. Chem.* 2010, 75, 4, 1228-1234.
3. J. Hou, M.-H. Park, S. Zhang, Y. Yao, L.-M. Chen, J.-H. Li, Y. Yang, *Macromolecules* 2008, 41, 16, 6012-6018.
4. A. K. Mishra, S. Vaidyanathan, H. Noguchi, F. Dötz, S. Köhler, M. Kastler, PCT Int. Appl. (2009), 8 pp. WO 2010079064.
5. P. Frère, J.-M. Raimundo, P. Blanchard, J. Delaunay, P. Richomme, J.-L. Sauvajol, J. Orduna, J. Garin, J. Roncali, *J. Org. Chem.* 2003, 68, 19, 7254-7265.

WORKING EXAMPLE 10

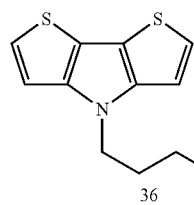
36

1. BuLi
2. N-Formylpiperidine
   THF
3. NH₄Cl

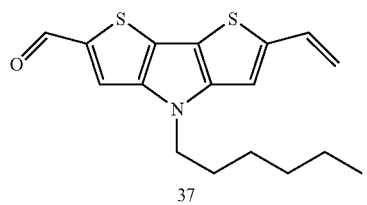
37

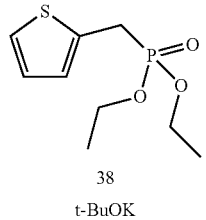
38
t-BuOK
Toluene

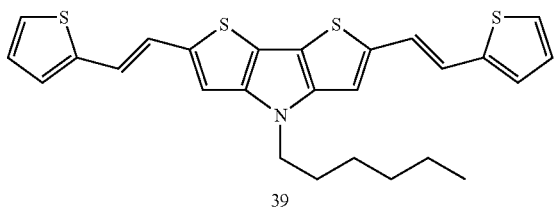
39

POCl3, DMF
DCM

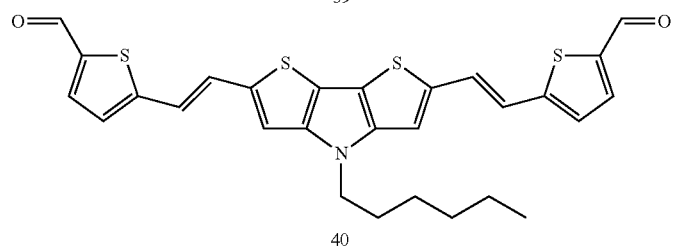
40
Mixture of cis/trans isomers

Malononitrile
piperidine
DCM

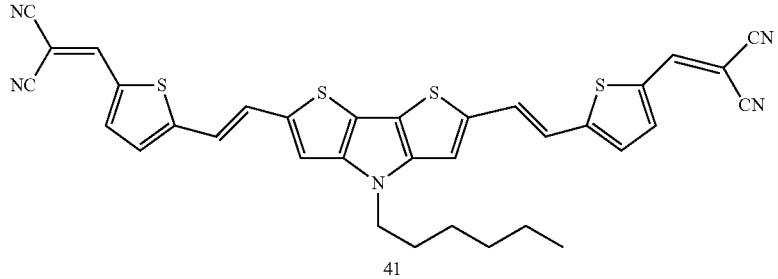
41
Mixture of cis/trans isomers

4-Hexyl-4H-dithieno[3,2-b;2',3'-d]pyrrol-2,6-dicarbaldehyde (37)

To a solution of 4-hexyl-4H-dithieno[3,2-b;2',3'-d]pyrrole (36) (1.100 g, 4.18 mmol) in 126 ml of dry THF are added, at −78° C. under argon over a period of 20 minutes, n-BuLi (1.6 M in hexanes; 5.5 ml, 8.79 mmol). After the addition, the mixture was stirred at −78° C. for a further 90 minutes and then warmed to room temperature. After stirring at RT for a further 1 hour, the mixture was cooled again to −78° C. and N-formylpiperidine (1.045 g, 9.24 mmol) was added rapidly by means of a syringe. The mixture was stirred at −78° C. for a further 30 minutes and then brought to RT within 4 hours. Stirring under argon continued overnight. The reaction was stopped by adding a saturated NH₄Cl solution (47 ml). After continuing to stir at RT for 15 minutes, the mixture was transferred to a separating funnel and extracted with dichloromethane (3×80 ml). The combined organic phases were washed with water (2×30 ml) and dried over Na₂SO₄. After filtration and removal of the solvent, the crude product was purified by means of flash chromatography (silica gel, DCM as eluent, $R_f$=0.25). After the product fractions had been combined and the solvent had been removed, a yellow solid was isolated (533 mg, 1.67 mmol; 40%). 1H NMR (CDCl₂); δ=9.88 (s, 2H, CHO), 7.63 (s, 2H, Th—H), 4.21 (t, 2H, CH₂), 1.85 (m, 2H, CH₂), 1.12 (m, 6H, 3×CH₂), 0.80 (t, 3H, CH₃).

4-Hexyl-2,6-bis(E)-2-thiophen-2-ylvinyl)-4H-dithieno[3,2-b;2',3'-d]pyrrole (39)

Dialdehyde (37) (0.320 g, 1.00 mmol) and diethyl (2-thienylmethyl)phosphonate (38) (1.000 g, 4.27 mmol) (purchased from metina (Sweden)) were dissolved in 100 ml of anhydrous and degassed toluene. After the mixture had been heated to 110° C., t-BuOK (0.900 g, 8.00 mmol) was added in 4 portions (0.250 g each) with continued stirring under argon within 15 minutes. The mixture was refluxed while stirring for a further 10 hours. After cooling to RT, the reaction was quenched by adding 50 ml of 0.2 M HCl (10 mmol) and continuing to stir for 15 minutes. The mixture was transferred into a 1 l beaker and neutralized by adding saturated NaHCO₃ solution. Finally, the mixture was transferred to a separating funnel and the product was extracted with toluene (3×80 ml). The combined organic phases were washed with water (2×20 ml) and dried over Na₂SO₄. After removal of the solvent and drying, a red solid (0.480 mg, 1.00 mmol; 100%) was obtained. 1H NMR(C2D$_2$Cl$_4$, 100° C.; δ=7.14-6.87 (m, 12H, Th—H & vinyl-H), 4.14-4.04 (m, 2H, CH$_2$), 1.87-1.81 (m, 2H, CH$_2$), 1.30-1.20 (m, 6H, 3×CH$_2$), 0.84 (m, 3H, CH$_3$); MALDI-MS (m/z): 479.2 (M$^+$). The crude product was used for the next step without further purification.

Dialdehyde (40)

Phosphorus oxychloride (1.1 ml, 12.2 mmol) was added to a solution of dimethylformamide (1.04 ml, 13.4 mmol) in dichloromethane (DCM, 13.8 ml), and the mixture was stirred under argon for 2 hours. To a solution of 39 (479.8 mg, 1.00 mmol) in DCM (18.3 ml) was added dropwise a portion of the above-described Vilsmeier reagent (11.6 ml, 10.0 mmol). The mixture was refluxed under argon for 48 hours. After cooling to RT, the solution was admixed with a saturated NaHCO$_3$ solution (61 ml) and the mixture was stirred for 2 hours. After transfer to a separating funnel and addition of DCM (80 ml), the organic phase was removed and the aqueous phase was extracted three times with DCM (30 ml). The combined organic phases were washed with water (2×20 ml) and dried over Na$_2$SO$_4$. After removal of the solvent by rotary evaporation and drying, the product was obtained as a mixture of cis and trans isomers as a red solid (528 mg, 0.987 mmol; 99%). 1H NMR(C2D$_2$Cl$_4$, 100° C.; δ=9.93-9.58 (m, 2H, CHO), 7.80-7.60 (m, 4H, Th—H), 7.40-7.05 (m, 6H, Th—H & vinyl-H), 4.30-4.10 (m, 2H, CH$_2$—N), 2.05-1.90 (m, 2H, CH$_2$), 1.50-1.30 (m, 6H, 3×CH$_2$), 0.84 (m, 3H, CH$_3$); MALDI-MS (m/z): 535.1 (M$^+$); UV-vis (DCM): 518 nm.

2-Cyano-3-{5-[(E)-2-(6-{(E)-2-[5-(2,2-dicyanovinyl)thiophen-2-yl]vinyl}-4-hexyl-4H-dithieno[3,2-b;2',3'-d]pyrrol-2-yl)vinyl]thiophen-2-yl}acrylonitrile (41)

A mixture of dialdehyde 40 (0.520 g, 0.97 mmol), malonitrile (0.513 mg, 7.76 mmol) and piperidine (0.083 mg, 0.1 ml, 0.97 mmol) in 1,2-dichloroethane (95 ml) was refluxed under argon for 46 hours. The progress of the reaction was monitored by means of UV-vis spectroscopy (DCM, =577 nm, shoulder at □=545 nm). Continuation of the Knoevenagel reaction for a further 24 hours after another addition of malononitrile (0.133 g, 2.00 mmol) and piperidine (0.01 ml, 0.01 mmol) did not give any change in the UV-vis spectrum. Consequently, the reaction was stopped and the solvent was drawn off by means of a rotary evaporator. The residue was admixed with water (50 ml) and refluxed for 2 hours. After hot filtration by means of a suction filter, the filter residue was dried and then subjected to a Soxhlet extraction with methanol. The drying was followed by successive extraction with toluene and chlorobenzene. The precipitated solids from both extractions (toluene: 0.170 g, shiny bronze solid; chlorobenzene; 0.400 g, shiny dark bronze solid) gave the same UV-vis spectrum recorded in DCM. Due to poor solubility in all organic solvents, correct assignment of the 1H NMR signals was not possible. MALDI-MS (m/z): 631.2 (M$^+$); UV-vis (DCM): 577 nm, 545 nm(sh).

WORKING EXAMPLE 11

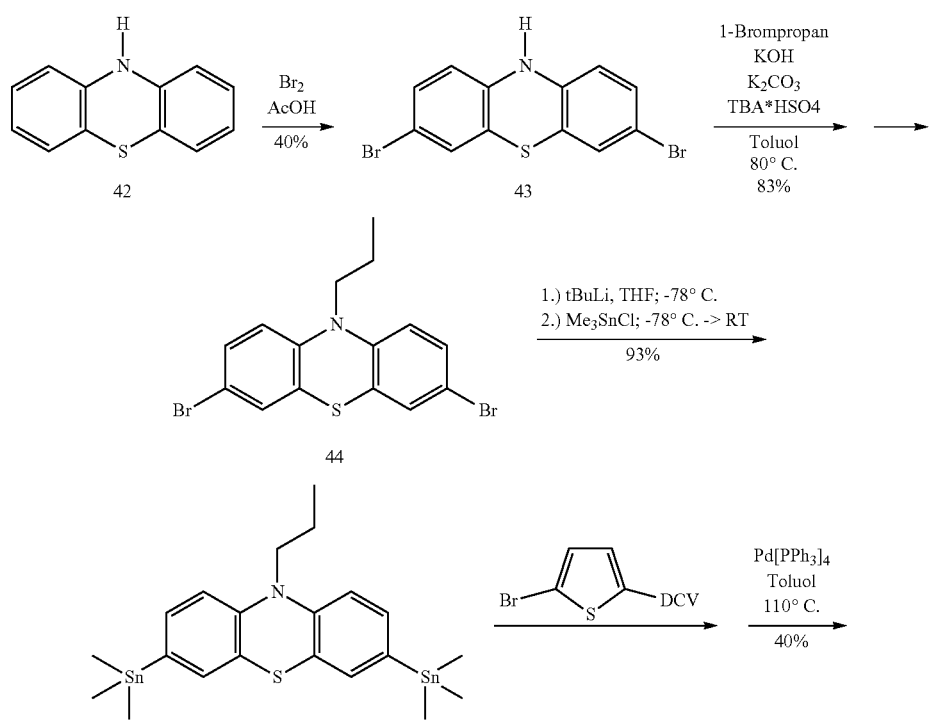

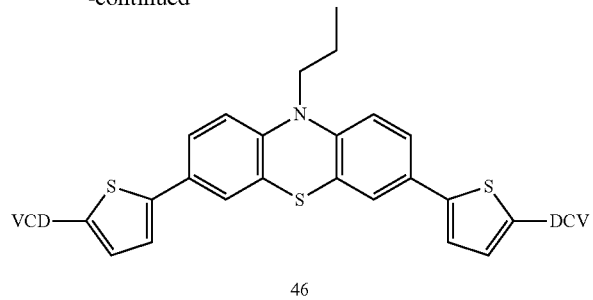

3,7-Dibromo-10H-phenothiazine (43)

prepared from 10H-phenothiazine (42) in 40% yield by a literature method (C. Bodea, M. Raileanu, Ann. Chim. (Paris), 1960, 631, 194-197).

1H NMR (acetone-d6): 8.22 (br.s, 1H), 7.24 (d, 2H), 7.22 (s, 2H), 6.76 (d, 2H).

3,7-Dibromo-10-propyl-10H-phenothiazine (44)

synthesized in 83% yield from 3,7-dibromo-10H-phenothiazine (43) by a modified literature protocol (H. Oka, J. Mater. Chem., 2008, 18, 1927-1934).

1H NMR (CDCl$_3$): 7.26 (d, 2H), 7.25 (s, 2H), 6.69 (d, 2H), 3.75 (t, 2H), 1.80 (m, 2H), 1.00 (t, 3H).

10-Propyl-3,7-bis(trimethylstannyl)-10H-phenothiazine (45)

prepared from (44) by the above-described general method for preparation of bis(trimethylstannyl) compounds.

1H NMR (CDCl$_3$): 7.60 (m, 4H), 7.20 (d, 2H), 4.15 (m, 2H), 2.19 (m, 2H), 1.35 (t, 3H), 0.60 (s, 18H).

2-Cyano-3-(5-{7-[5-(2,2-dicyanovinyl)thiophen-2-yl]-10-propyl-10H-phenothiazin-3-yl}thiophen-2-yl)acrylonitrile (46)

prepared in 40% yield via Stille coupling from (45) by the above-described general method.

m.p.: 290° C.

1H NMR (TCE-d2 at 375° C.): 7.79 (s, 2H), 7.77 (d, 2H), 7.54 (d, 2H), 7.47 (s, 2H), 7.40 (d, 2H), 6.96 (d, 2H), 3.94 (t, 2H), 1.93 (m, 2H), 1.13 (t, 3H).

UV-VIS: 574 nm (film 30.0 nm, A$_{max}$ 0.28); 495 nm (THF, A$_{max}$ 0.61).

WORKING EXAMPLE 12

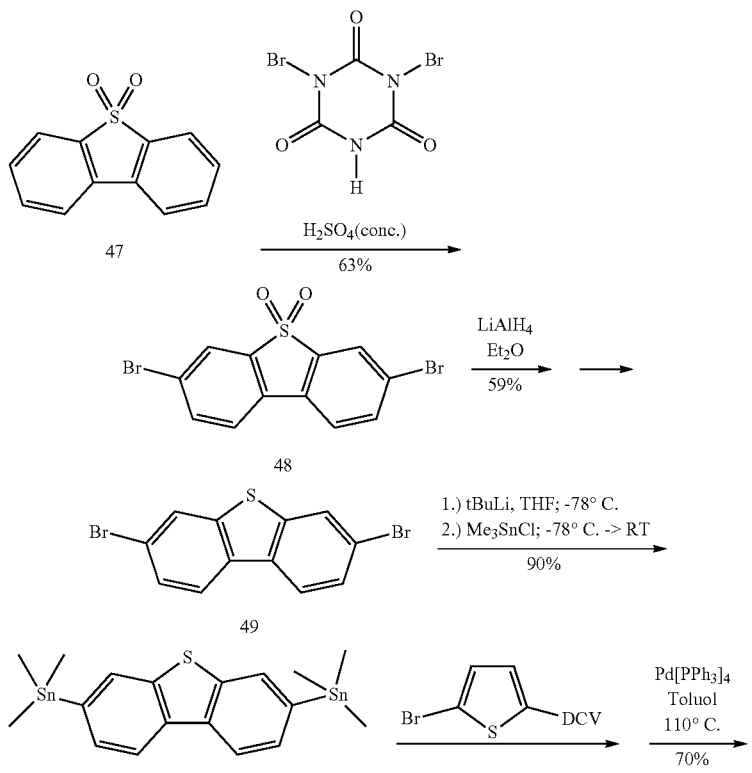

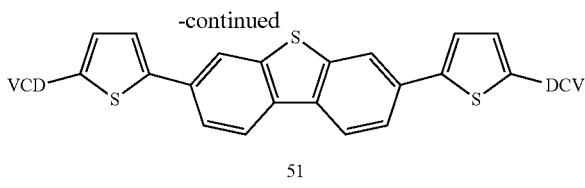

DCV-T-PhTPh-T (51)

3,7-Dibromodibenzothiophene 5,5-dioxide (48)

prepared from dibenzothiophene dioxide (47) in 63% yield by a literature method (see H. Sirringhaus, R. H. Friend, C. Wang et al., J. Mater. Chem., 1999, 9, 2095-2101).

1H NMR (DMSO-d6): 8.71 (s, 2H), 8.50 (d, 2H), 8.38 (d, 2H).

3,7-Dibromodibenzothiophene (49)

prepared from 3,7-dibromodibenzothiophene dioxide (48) in 59% yield by a literature protocol (see H. Sirringhaus, R. H. Friend, C. Wang et al., J. Mater. Chem., 1999, 9, 2095-2101).

1H NMR ($CDCl_3$): 7.97 (d, 2H), 7.96 (d, 2H), 7.56 (dd, 2H).

3,7-bis(Trimethylstannyl)dibenzothiophene (50)

prepared from 49 in 90% yield by the above-detailed general protocol for synthesis of bistrimethylstannyl compounds.

1H NMR ($CDCl_3$): 8.12 (d, 2H), 7.98 (s, 2H), 7.56 (d, 2H), 0.35 (s, 18H).

2-Cyano-3-(5-{7-[5-(2,2-dicyanovinyl)thiophen-2-yl]dibenzothiophen-3-yl}thiophen-2-yl)acrylonitrile (51)

synthesized in 70% yield by the above-detailed general protocol for Knoevenagel condensations.

m.p.: 353° C.

1H NMR (DMSO-d6 at 375 K): 8.57 (d, 4H), 8.48 (d, 2H), 8.02 (s, 2H), 7.94 (m, 4H)

UV-VIS: 476 nm (film 30.0 nm, $A_{max}$ 0.55)

WORKING EXAMPLE 13

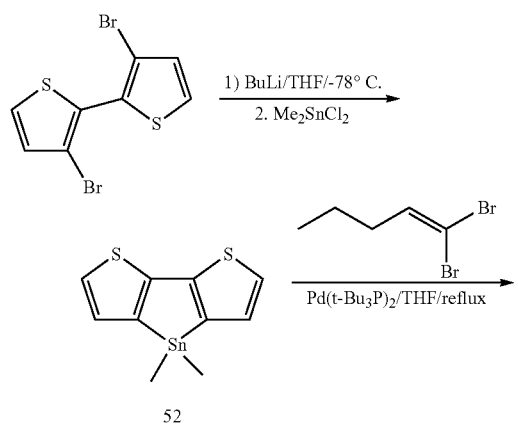

7,7-Dimethyl-7H-3,4-dithia-7-stannacyclopenta[a]pentalene (52)

2.0 g (6.17 mmol) of dibromodithiophene were dissolved in 120 ml of anhydrous diethyl ether and cooled to −78° C. under argon. N-Butyllithium (8 ml, 12.34 mmol), 1.6 molar in hexane) was added gradually. The reaction mixture was stirred at −78° C. for 2 hours and then warmed to RT. A solution of dimethylstannyl dichloride (1.42 g, 6.46 mmol) in 30 ml of dry diethyl ether was added and the mixture was stirred under argon for 8 hours. All solvents were removed by rotary evaporation and the residue was taken up in hexane. The suspension thus obtained was filtered through Celite and the solvent was removed to obtain 1.27 g of compound 1 (66% yield). GC-MS m/z 314 (11.09 min).

4-Butylidene-4H-cyclopenta[2,1-b;3,4-b']dithiophene (53)

500 mg (1.6 mmol) of 52 and 364 mg (1.6 mmol) of dibromopentene were dissolved in 32 ml of freshly distilled THF, and 42 mg (80 µmol) of bis(tri-tert-butylphosphine)palladium(0) were added. The reaction mixture was refluxed while stirring for 8 hours. THF was removed by rotary evaporation and the residue was taken up in n-hexane. The crude product was purified by means of column chromatography (n-hexane as the eluent (Rf=0.4)) to obtain 115 mg of the target compound 53 (37% yield). GC-MS m/z 232 (18.10 min).

4-Butylidene-2,6-bis(trimethylstannyl)-4H-cyclopenta[2,1-b;3,4-b']dithiophene (54)

Compound 54 was synthesized in 69% yield by the above general method.

3-(5-{4-Butylidene-6-[5-(2,2-dicyanovinyl)thiophen-2-yl]-4H-cyclopenta[2,1-b;3,4-b']dithiophen-2-yl}thiophen-2-yl)-2-cyanoacrylonitrile (55)

Compound 55 was prepared by the above general protocol for Stille couplings. UV/vis: λmax (dichloromethane) 525 nm.

WORKING EXAMPLE 14

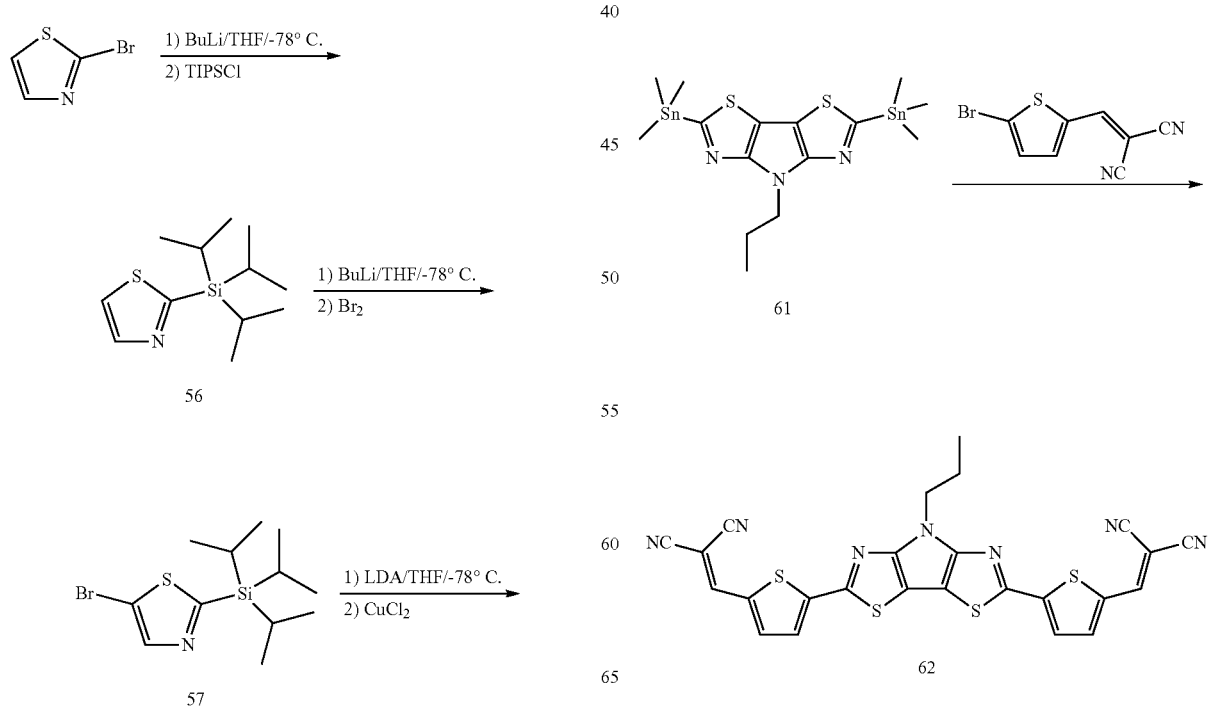

2-Triisopropylsilanylthiazole (56)

Compound 56 was prepared by a literature method (E. L. Stangeland, T. Sammakia, J. Org. Chem., 2004, 69, 2381-2385).

5-Bromo-2-triisopropylsilanylthiazole (57)

Compound 57 was prepared by a literature method (E. L. Stangeland, T. Sammakia, J. Org. Chem., 2004, 69, 2381-2385).

4,4'-Dibromo-2,2'-bis(triisopropylsilanyl)[5,5']bithiazolyl (58), 7-propyl-2,5-bis(triisopropylsilanyl)-7H-3,4-dithia-1,6,7-triazacyclopenta[a]pentalene (59) and 7-propyl-7H-3,4-dithia-1,6,7-triazacyclopenta[a]pentalene (60)

Compounds 58, 59 and 60 were likewise synthesized by a literature protocol (Y. A. Getmanenko, P. Tongwa, T. V. Timofeeva, S. R. Marder, Org. Lett., 2010, 12 (9), 2136-2139).

7-Propyl-2,5-bis(trimethylstannyl)-7H-3,4-dithia-1,6,7-triazacyclopenta[a]pentalene (61) and 2-cyano-3-(5-{5-[5-(2,2-dicyanovinyl)thiophen-2-yl]-7-propyl-7H-3,4-dithia-1,6,7-triazacyclopenta[a]pentalen-2-yl}thiophen-2-yl)acrylonitrile (62)

Compounds 61 (87% yield) and 62 (20.0 mg; 8% yield) were prepared by our above general method for Stille couplings. Compound 62: MALDI (m/z): 539.1; UV (film, 30 nm): 601 nm, $A_{max}$=0.49.

WORKING EXAMPLE 15

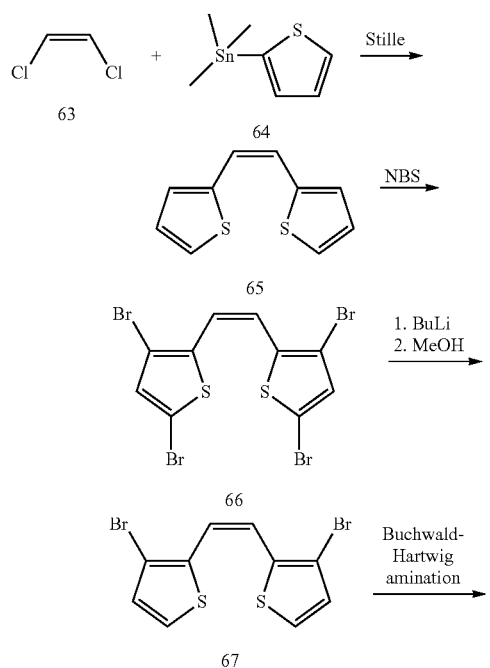

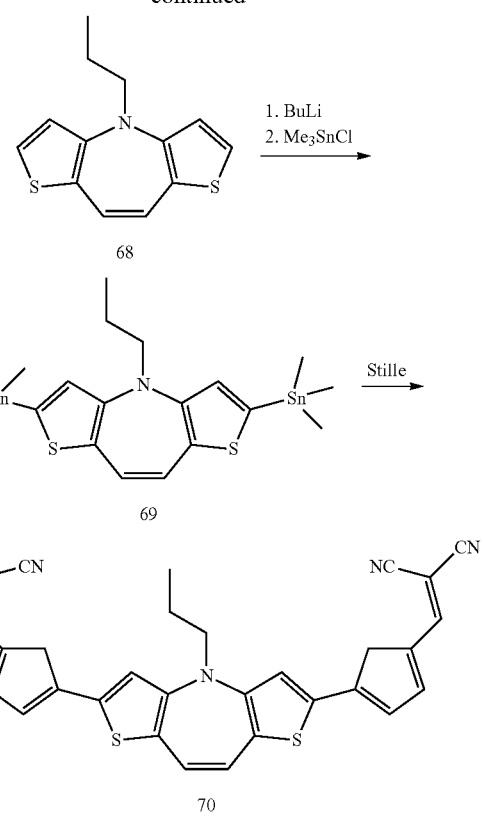

8-Propyl-8H-dithieno[3,2-b:2',3'-f]azepine (68)

Compounds 65, 66, 67 and 68 are synthesized by a literature protocol (C. Song, D. B. Walker, T. M. Swager, *Macromolecules* 2010, 43, 12, 5233-5237).

Dicyanovinyl Compound (70)

Compounds 69 and 70 are prepared by GM1 for Stille couplings.

WORKING EXAMPLE 16

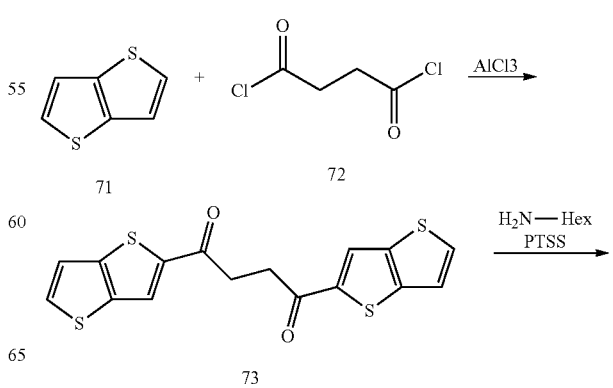

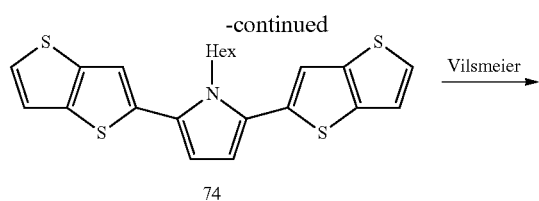

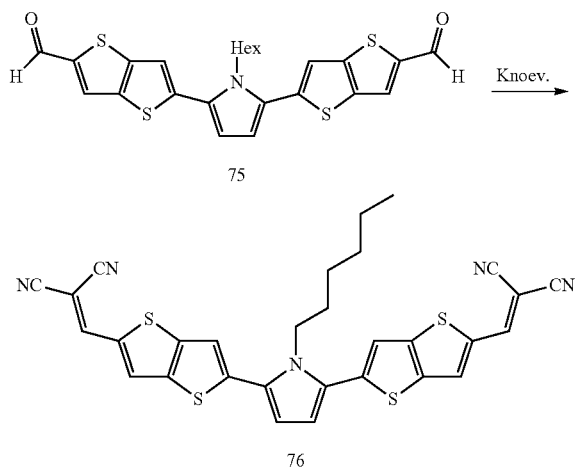

1-Hexyl-2,5-bis(thieno[3,2-b]thiophen-5-yl)pyrrole
(74)

Compounds 73 and 74 are synthesized by a literature protocol (L. I. Belen'kii, V. Z. Shirinyan, G. P. Gromova, A. V. Kolotaev, Y. A. Strelenko, S. N. Tandura, A. N. Shumskii, M. M. Krayushkin, *Chem. Heterocycl. Comp.* 2003, 39, 1570).

5-[5-(5-Formylthieno[3,2-b]thiophen-2-yl)-1-hexylpyrrol-2-yl]thieno[3,2-b]thiophene-2-carbaldehyde (75)

To a solution of 1-hexyl-2,5-bis(thieno[3,2-b]thiophen-5-yl)pyrrole (74) in dichloromethane is added a solution of phosphorus oxychloride and DMF in DCM. The reaction mixture is refluxed for 16 h, then sat. sodium hydrogencarbonate solution is added and the mixture is stirred at room temperature for 2 h. After phase separation, the organic phase is dried over sodium sulfate. After the solvents have been distilled off, the residue is recrystallized from toluene to obtain the product.

2-[[2-[5-[5-(2,2-Dicyanovinyl)thieno[3,2-b]thiophen-2-yl]-1-hexylpyrrol-2-yl]thieno[3,2-b]thiophen-5-yl]methylene]propanedinitrile (76)

A solution of dialdehyde 75, malonitrile and piperidine in 1,2-dichloroethane is refluxed for 48 h. After the solvent has been distilled off, the residue is suspended in water and refluxed for 2 h. The crude product is filtered, washed with water and methanol, and dried under reduced pressure. The residue is recrystallized from chlorobenzene to obtain the product.

WORKING EXAMPLE 17

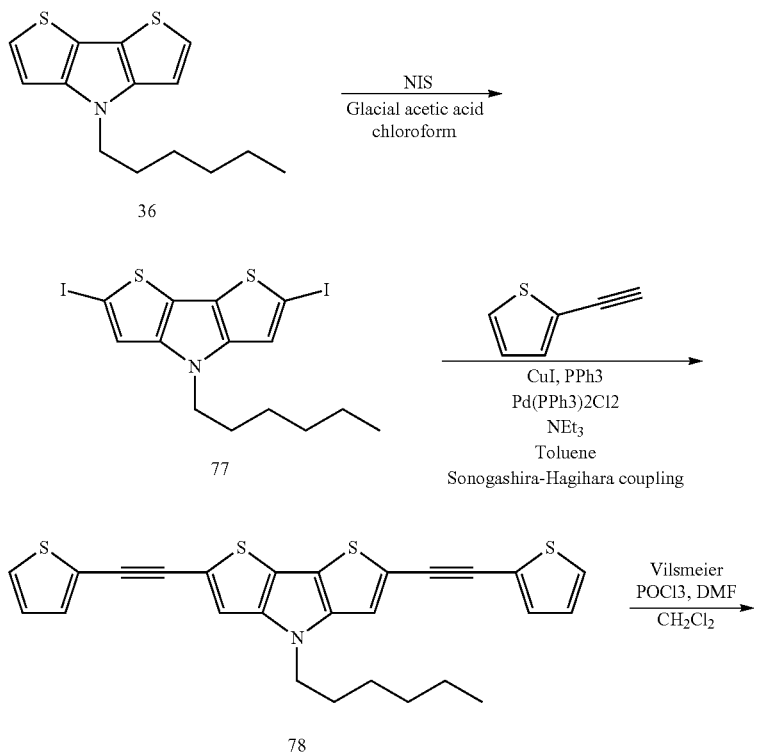

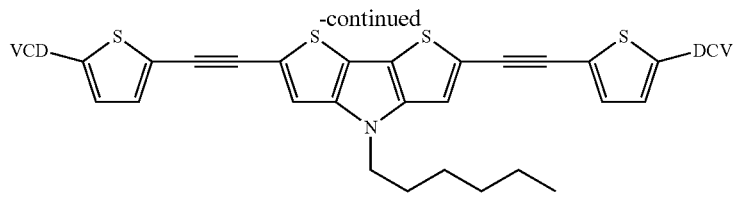

80

4-Hexyl-2,6-diiodo-4H-dithieno[3,2-b;2',3'-d]pyrrole (77)

To a solution of 4-hexyl-4H-dithieno[3,2-b;2',3'-d]pyrrole (36) (0.500 g, 1.90 mmol) in a mixture consisting of chloroform (12 ml) and glacial acetic acid (12 ml), while stirring, with exclusion of light and under argon, at 0° C. (ice cooling), N-iodosuccinimide (1.068 g, 4.75 mmol) is added in 5 portions to 214 mg each time. The period between the additions was 7 minutes each time. The stirring was continued overnight at 0-4° C. under argon with exclusion of light, and then the mixture was warmed to RT. After continuing to stir for 2 hours, the mixture was transferred to a separating funnel and admixed with further water (50 ml) and chloroform (100 ml). After shaking, the mixture was separated and the aqueous phase was extracted three times more with 50 ml each time of chloroform. The combined organic phases were washed successively with saturated aqueous solutions of $NaHCO_3$ and $Na_2S_2O_3$ (30 ml of each) and with water (2×30 ml). After drying over $Na_2SO_4$, the mixture was filtered and the solvent was removed by rotary evaporation. The residue was purified by means of flash column chromatography (silica gel, n-hexane as the eluent ($R_f$=0.37)). After the solvent had been removed by rotary evaporation, 0.718 g (74% yield) of yellow crystals of 2 were obtained. 1H NMR ($CDCl_2$-$CDCl_2$): δ=7.21 (s, 2H, Th—H), 4.07 (t, 2H, $CH_2$—N), 1.80 (t, 2H, $CH_2$), 1.29 (m, 6H, 3×$CH_2$), 0.88 (t, 3H, $CH_2$).

4-Hexyl-2,6-bis(thiophen-2-ylethynyl)-4H-dithieno [3,2-b;2',3'-d]pyrrole (78)

The compound was synthesized in a modified procedure by the above-described general method for Sonogashira-Hagihara couplings.

A carefully dried screw top pressure vessel was initially charged successively with absolute toluene (25 ml) and abs. triethylamine (3.359 g, 4.6 ml, 33.2 mmol). Argon was bubbled through for 30 minutes (degassing). In a gentle opposing argon stream, 2-ethynylthiophene (1.000 g, 9.25 mmol), compound 77 (0.4764 g, 0.92 mmol), $Pd(PPh_3)_2Cl_2$ (0.0324 g, 0.046 mmol), CuI (0.0176 g, 0.09 mmol) and $PPh_3$ (0.0242 g, 0.09 mmol) were added successively. After digesting (degassing and argon flooding) 3 times and bubbling argon through for a further 10 minutes, the vessel was closed with the screw top and the mixture was stirred at 50° C. for 48 hours. After cooling, the mixture was transferred to a separating funnel and, after adding a further 20 ml of toluene, washed successively with water (15 ml), 30 ml each of sat. aq. $NH_4Cl$ solution, sat. aq. $NaHCO_3$ solution, sat. aq. NaCl solution and water. After drying over $Na_2SO_4$, the solvent was removed by rotary evaporation and 1.5743 g of a red solid were isolated. MALDI-MS (m/z): 475.3 ($M^+$). Approx. 30% of the target product was present in the crude product.

The syntheses to give bisaldehyde 79 via the Vilsmeier reaction and further to give 2-cyano-3-(5-{6-[5-(2,2-dicyanovinyl)thiophen-2-ylethynyl]-4-hexyl-4H-dithieno[3,2-b; 2',3'-d]pyrrol-2-ylethynyl}thiophen-2-yl)acrylonitrile 80 via Knoevenagel condensation are currently proceeding by the above protocol.

WORKING EXAMPLE 18

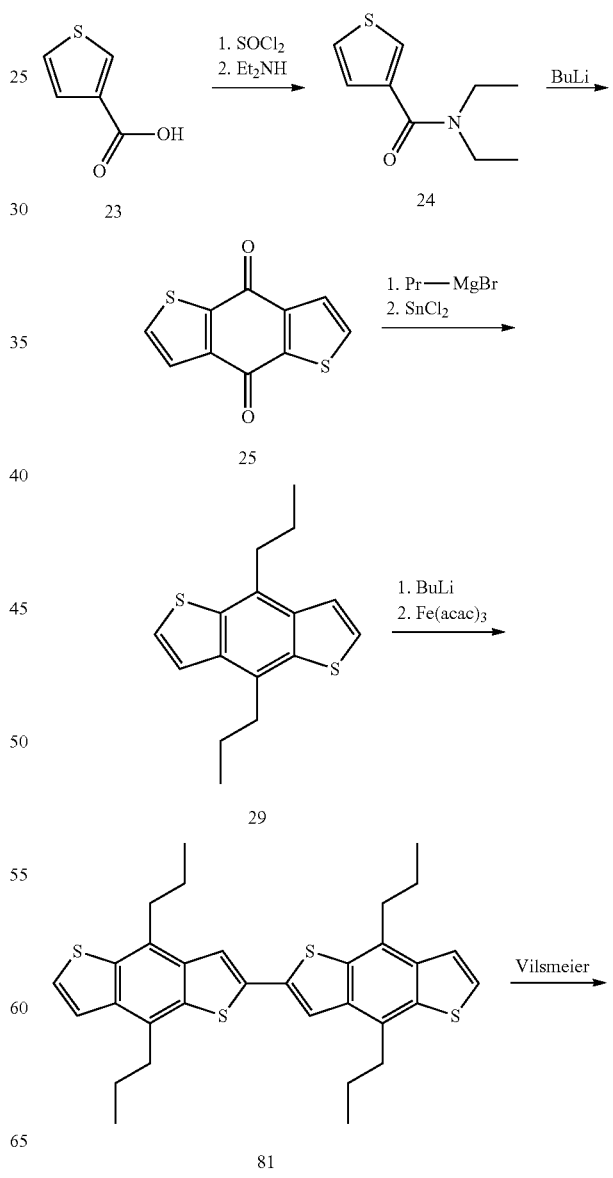

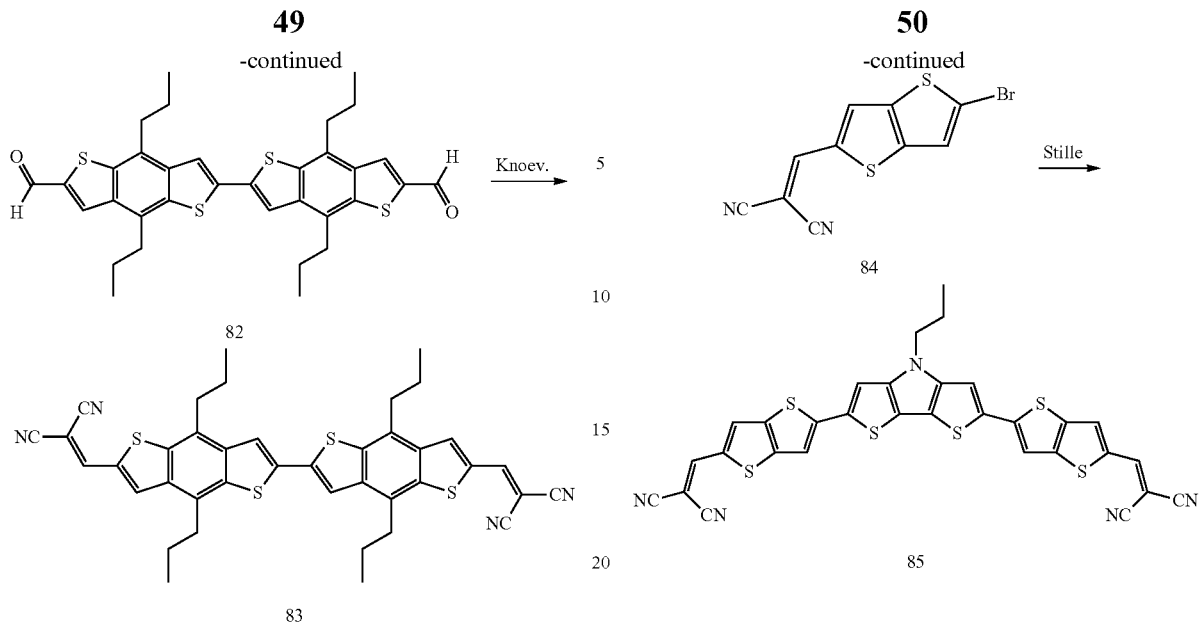

Bis(benzodithiophene) 81

Compound 81 is synthesized by a literature protocol (J. G. Laquindanum, H. E. Katz, A. J. Lovinger, A. Dodabalapur, *Adv. Mater.* 1997, 9, 1, 36-39).

Dialdehyde Compound 82

To a solution of bis(benzodithiophene) 81 in dichloromethane is added a solution of phosphorus oxychloride and DMF in DCM. The reaction mixture is refluxed for 16 h, then sat. sodium hydrogencarbonate solution is added and the mixture is stirred at room temperature for 2 h. After phase separation, the organic phase is dried over sodium sulfate. After the solvents have been distilled off, the residue is recrystallized from toluene to obtain the product.

Dicyanovinyl Compound 83

A solution of dialdehyde 82, malonitrile and piperidine in 1,2-dichloroethane is refluxed for 48 h. After the solvent has been distilled off, the residue is suspended in water and refluxed for 2 h. The crude product is filtered, washed with water and methanol, and dried under reduced pressure. The residue is recrystallized from chlorobenzene to obtain the product.

WORKING EXAMPLE 19

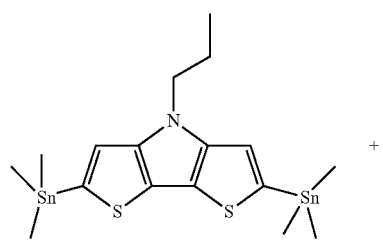

Dicyanovinyl Compound 85

Compound 85 is prepared according to GM1 for Stille couplings.

The above-described synthesis methods can also be used for synthesis of further inventive compounds. For example, the Stille coupling and the Knoevenagel reaction can be used with other units D or E for synthesis of further inventive oligomers. For instance, further organotin compounds R-SnR'3 and organic halides R''—X (X=halide) can be coupled to one another via the Stille coupling according to the following general formula:

where R and R'' are each organic radicals for linkage of the D, E and bd groups. As already described above, the acceptor groups can be introduced via reactions known to those skilled in the art, such as Gattermann, Gattermann-Koch, Houben-Hoesch, Vilsmeier/Vilsmeier-Haack, or Friedel-Crafts acylation.

In a further working example, a compound of the general formula IIIa is present as a constituent of an organic light-sensitive layer system in an inventive optoelectronic component. FIG. 4 shows such an inventive component in schematic form. This has the following layer sequence:

1.) Glass substrate 1,
2.) ITO base contact 2,
3.) Electron transport layer (ETL) 3,
4.) Organic light-sensitive layer system (10-200 nm) 4,
5.) Hole transport layer (HTL) 5,
6.) Top contact (e.g. gold) 6.

WORKING EXAMPLE 20

Component Comprising the Inventive Compound DCV-Fu-TPyT-Fu-Pr (3)

In a further working example, an MIP component consisting of a sample on glass with a transparent ITO top contact, a layer of Buckminster fullerene $C_{60}$, a 2:1 mixed layer of compound DCV-Fu-TPyT-Fu-Pr(3) of the formula:

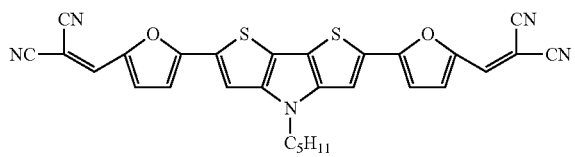

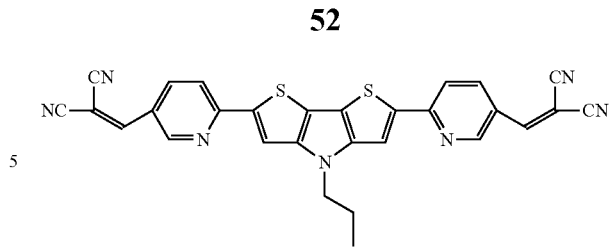

with C60, a p-doped hole transport layer and a layer of gold are produced.

Figure 5A:
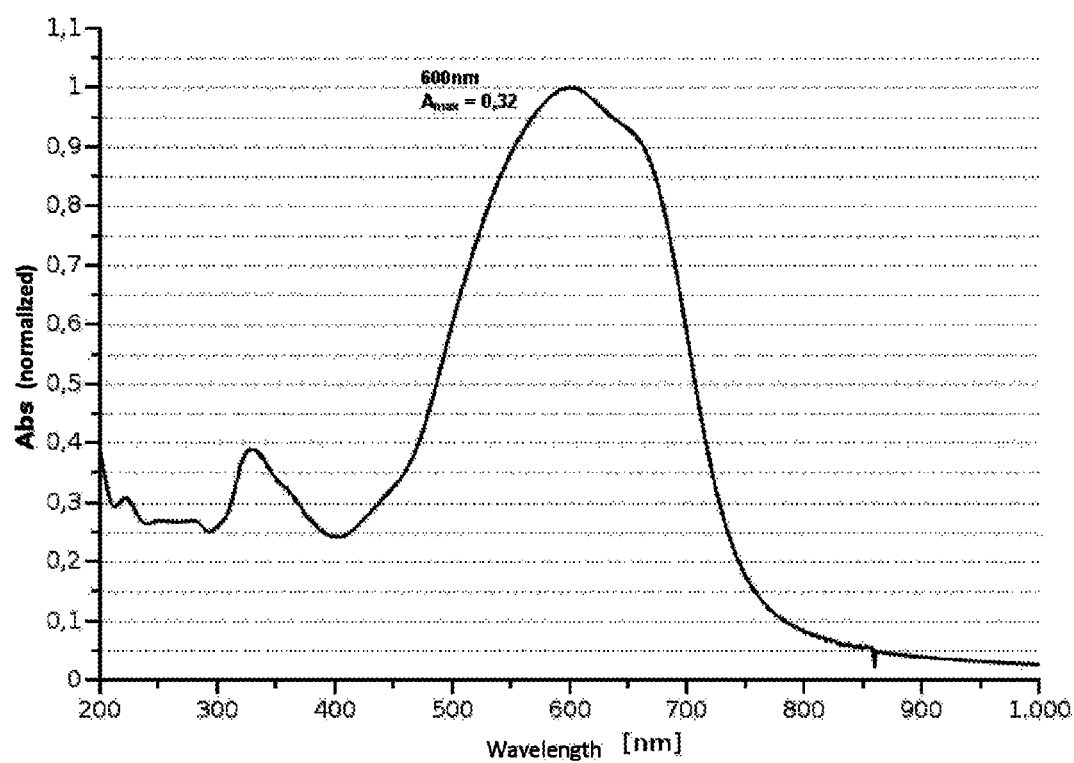
Figure 5B:
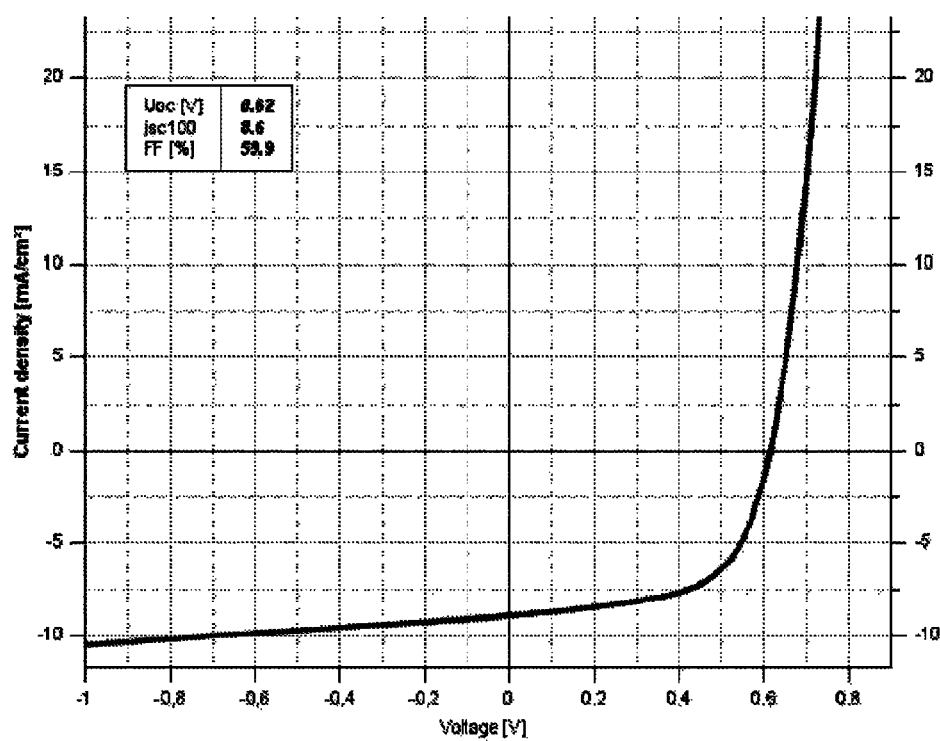

FIGS. 5A and 5B show a schematic diagram of an absorption spectrum of the compound and the current-voltage curve of this Mip cell comprising a mixed layer of compound DCV-Fu-TPyT-Fu-Pr(3) with $C_{60}$. The most important parameters such as the fill factor FF, the open-circuit voltage $U_{oc}$ and the short-circuit currents $j_{sc}$ show a well-functioning organic solar cell.

WORKING EXAMPLE 21

Component Comprising the Inventive Compound DCV-pH-TPyT-pH-Pr(3)

In a further working example, an Mip component consisting of a sample on glass with a transparent ITO top contact, a layer of Buckminster fullerene $C_{60}$, a 1:1 mixed layer of compound DCV-Ph-TPyT-Ph-Pr(3) having the following formula with C60

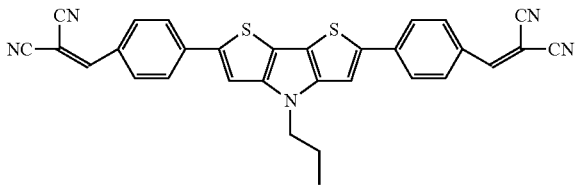 [SMILES: CCCn1c2cc(-c3ccc(C=C(C#N)C#N)cc3)sc2c2sc(-c3ccc(C=C(C#N)C#N)cc3)cc21]

a p-doped hole transport layer and a layer of gold are produced.

Figure 6A:
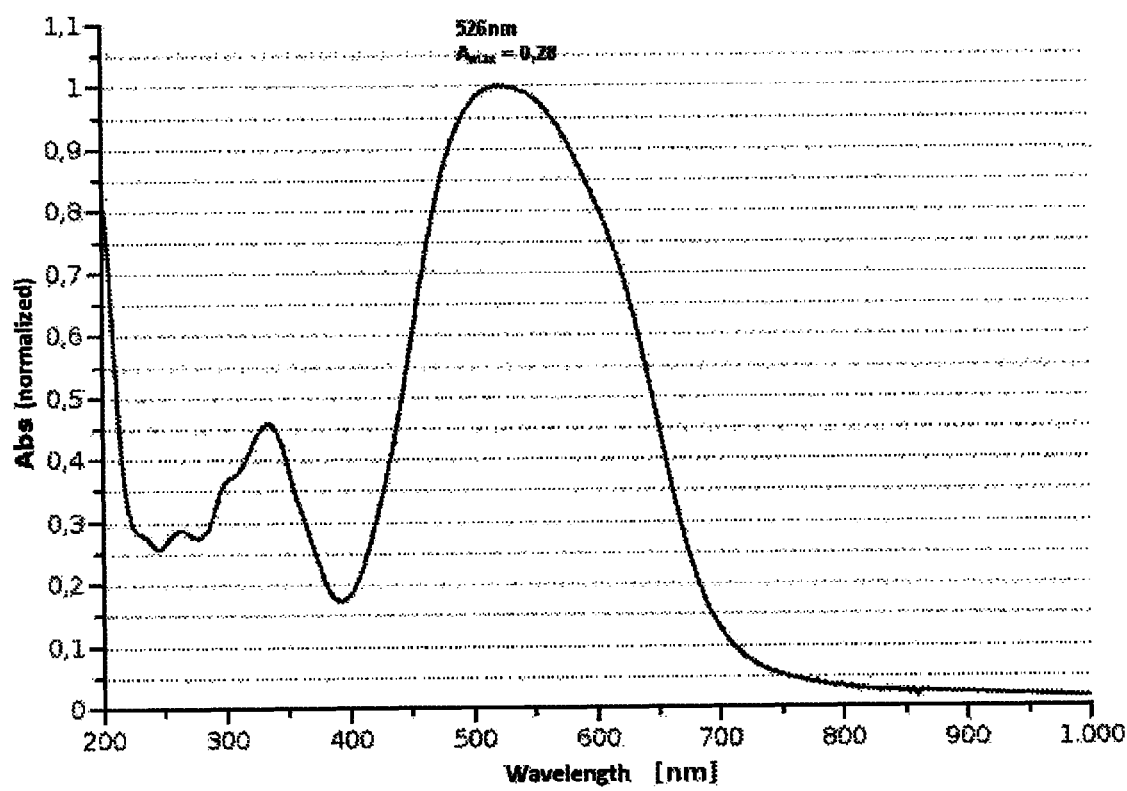
Figure 6B:
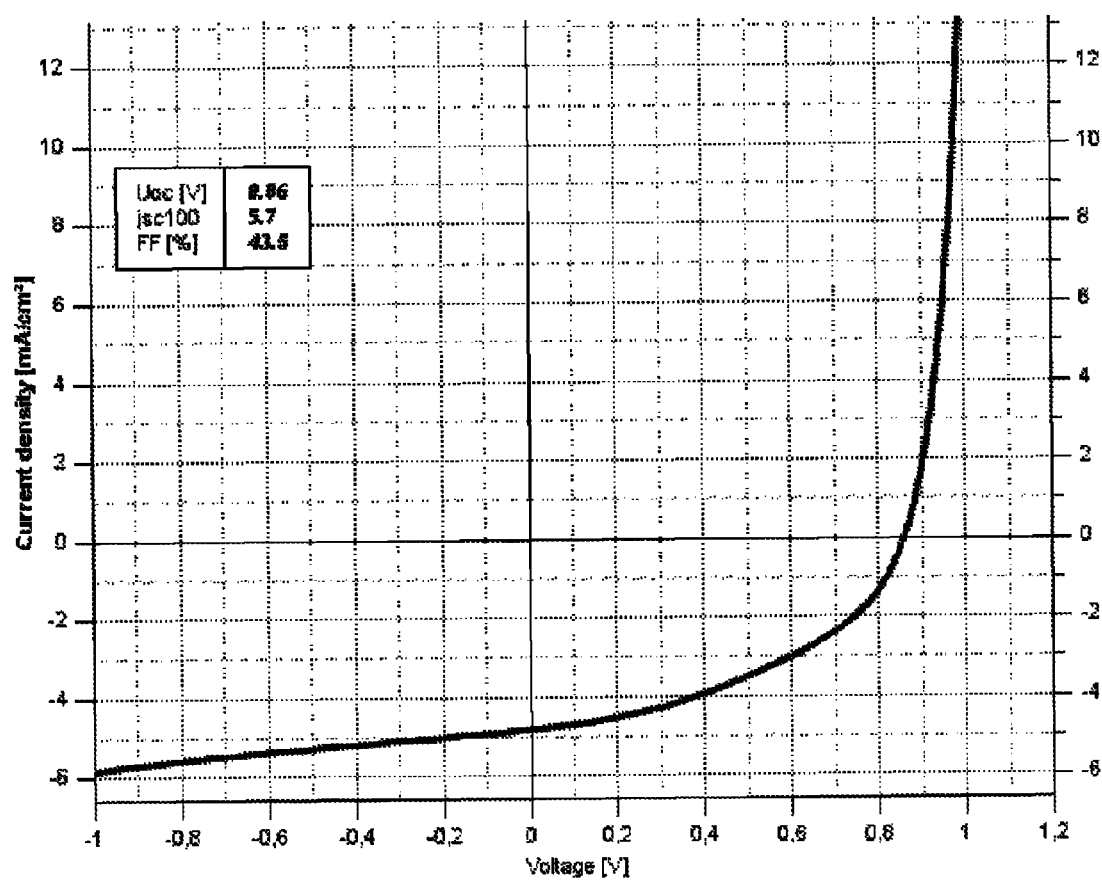

FIGS. 6A and 6B show a schematic diagram of an absorption spectrum of the compound and the current-voltage curve of this Mip cell comprising a mixed layer of compound DCV-Ph-TPyT-Ph-Pr(3) with C60. The most important parameters such as the fill factor FF, the open-circuit voltage $U_{oc}$ and the short-circuit current $j_{sc}$ show a functioning organic solar cell.

WORKING EXAMPLE 22

Component Comprising the Inventive Compound DCV-Pyr-TPyT-Pyr-Pr(3)

In a further working example, an MIP component consisting of a sample on glass with a transparent ITO top contact, a layer of Buckminster fullerene $C_{60}$, a 2:1 mixed layer of compound DCV-Pyr-TPyT-Pyr-Pr(3) having the following formula with C60 a p-doped hole transport layer and a layer of gold are produced.

Figure 7A:
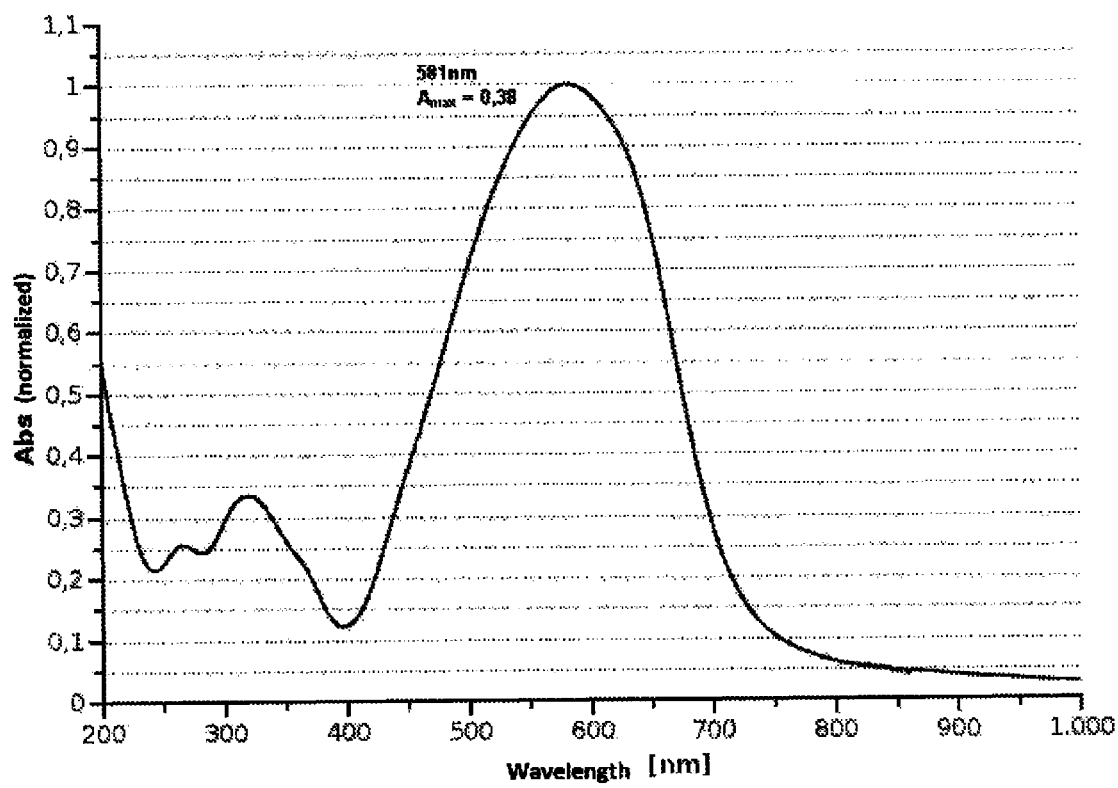
Figure 7B:
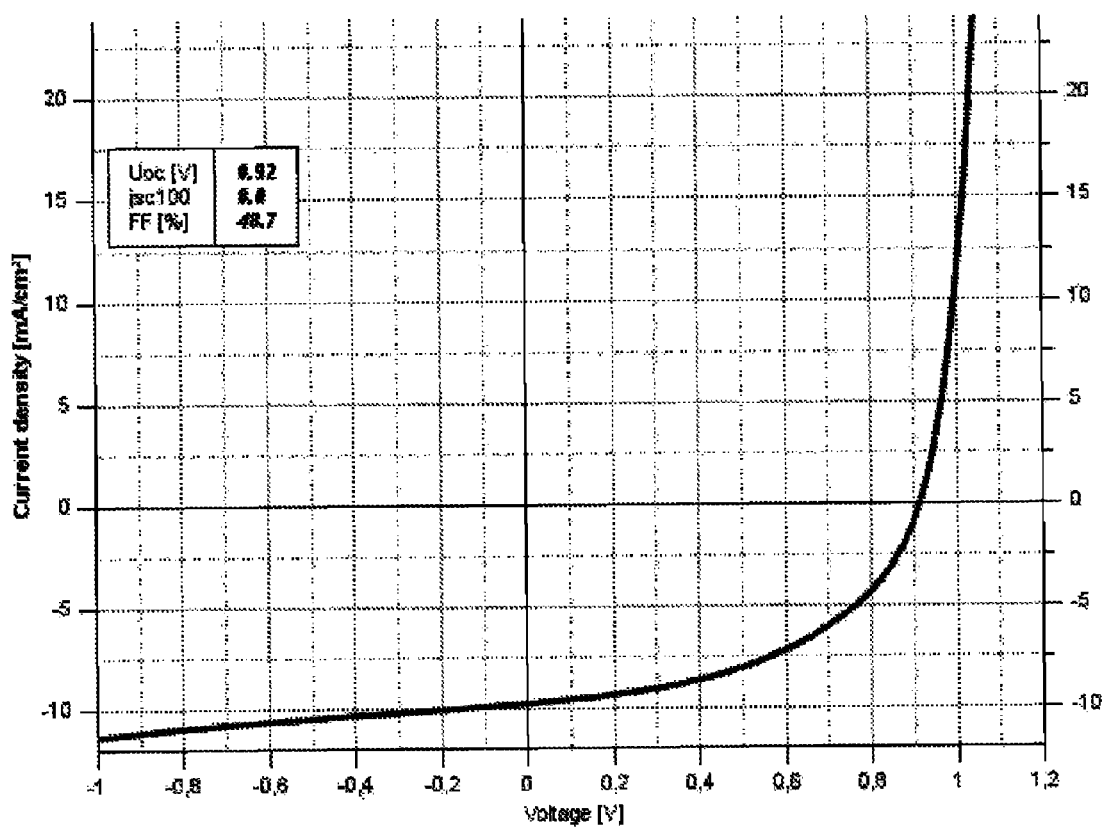

FIGS. 7A and 7B show a schematic diagram of an absorption spectrum of the compound and the current-voltage curve of this Mip cell comprising a mixed layer of compound DCV-Pyr-TPyT-Pyr-Pr(3) with C60. The most important parameters such as the fill factor FF, the open-circuit voltage $U_{oc}$ and the short-circuit current $j_{sc}$ show a well-functioning organic solar cell.

WORKING EXAMPLE 23

Component Comprising the Inventive Compound DCV-T-PhTaPh-T-Pr(3)

In a further working example, an MIP component consisting of a sample on glass with a transparent ITO top contact, a layer of Buckminster fullerene $C_{60}$, a layer of compound DCV-T-PhTaPh-T-Pr(3)

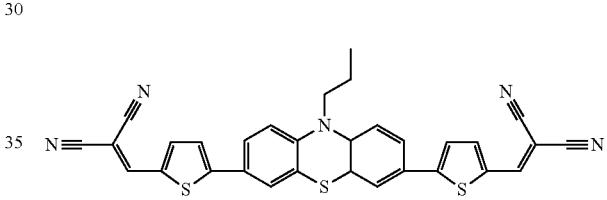

a p-doped hole transport layer and a layer of gold are produced.

Figure 8A:
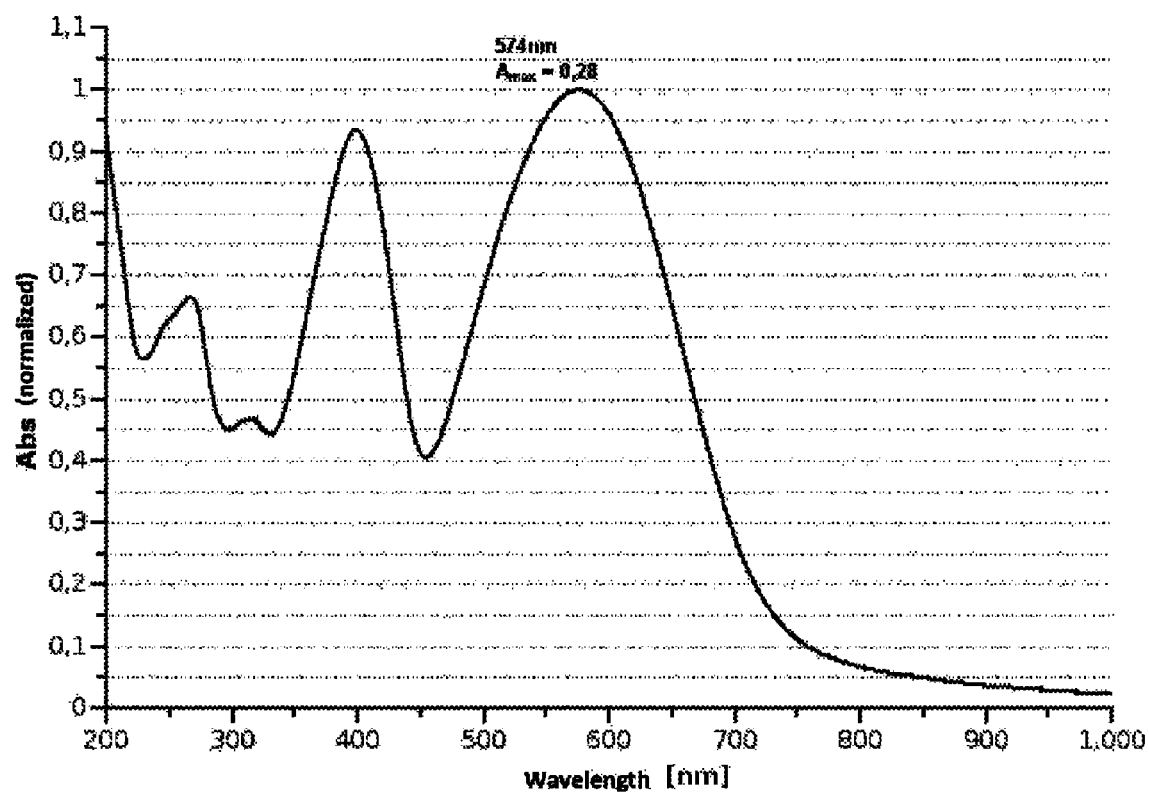
Figure 8B:
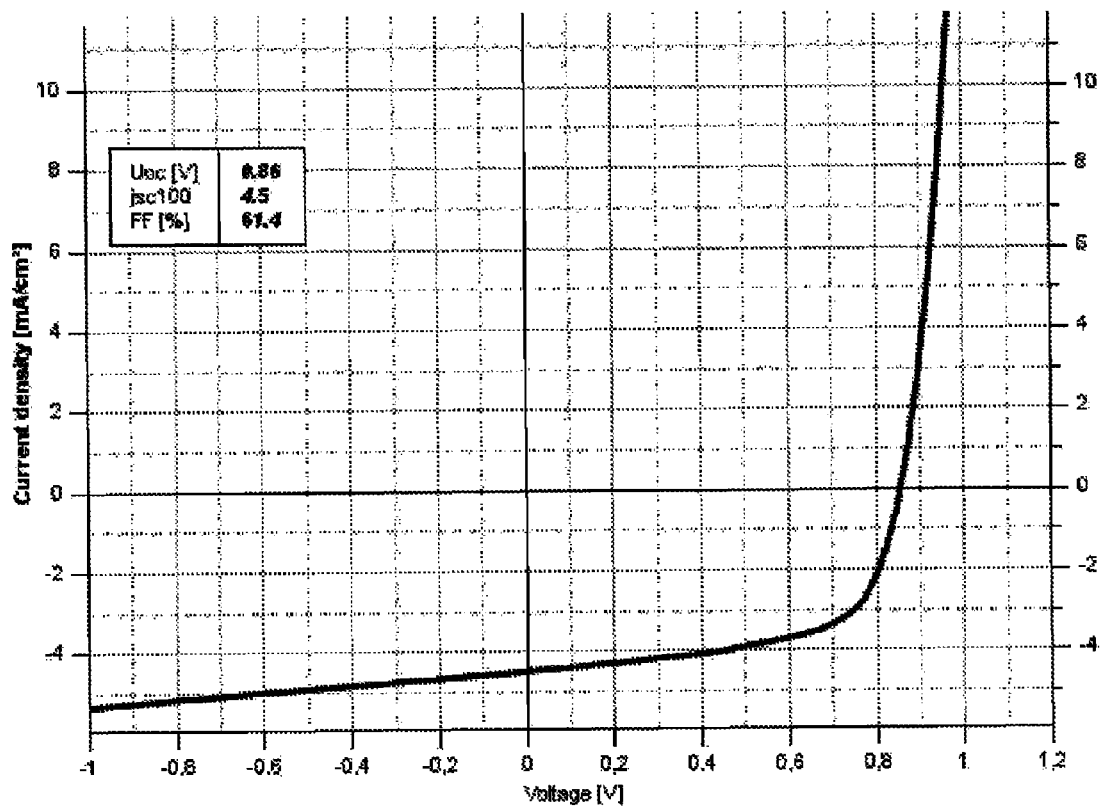

FIGS. 8A and 8B show a schematic diagram of an absorption spectrum of the compound and the current-voltage curve of this Mip cell comprising a layer of DCV-T-PhTaPh-T-Pr(3). The most important parameters such as the fill factor FF, the open-circuit voltage $U_{oc}$ and the short-circuit current $j_{sc}$ show a well-functioning organic solar cell.

WORKING EXAMPLE 24

Component Comprising the Inventive Compound DCV-TzPyTz-Pr2(3,3)

In a further working example, an MIP component consisting of a sample on glass with a transparent ITO top contact, a layer of Buckminster fullerene $C_{60}$, a 1:1 mixed layer of compound DCV-TzPyTz-Pr2(3,3) with C60

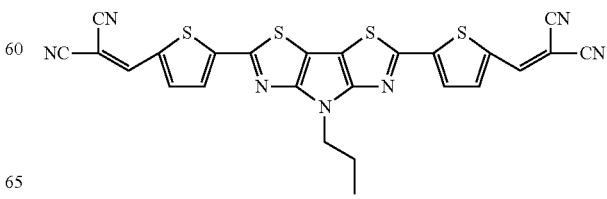

a p-doped hole transport layer and a layer of gold are produced.

Figure 9A:
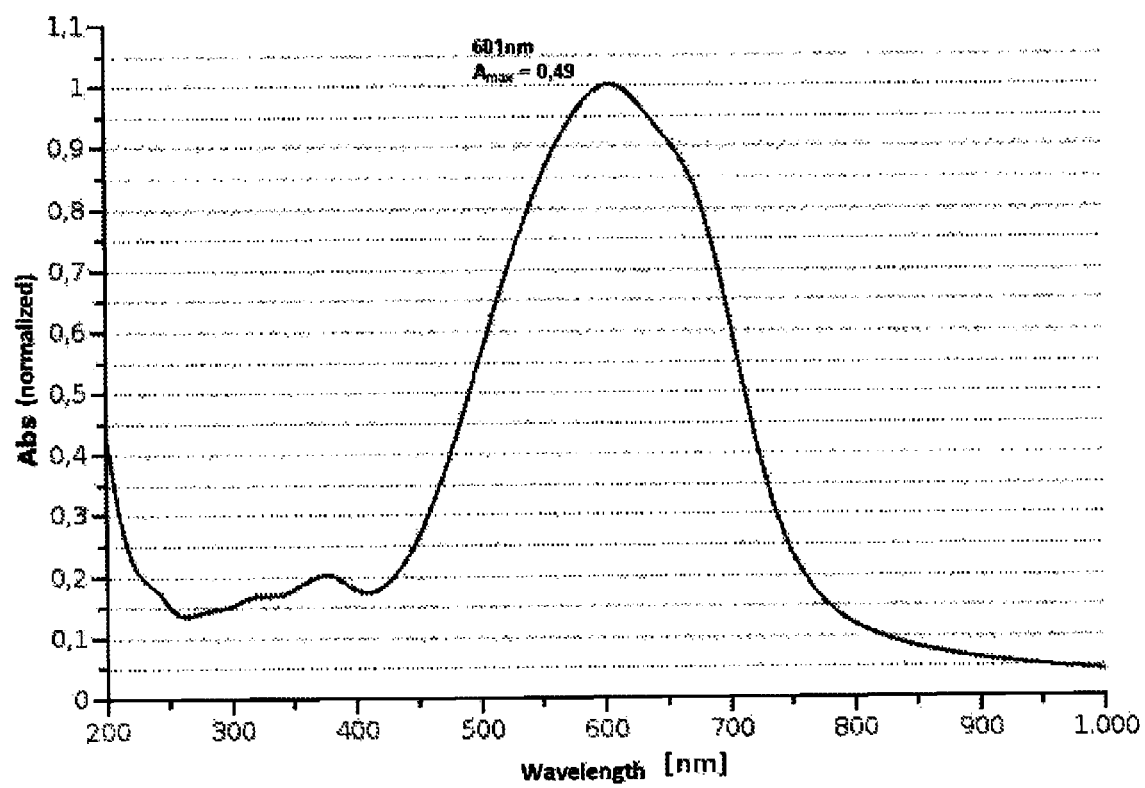
Figure 9B:
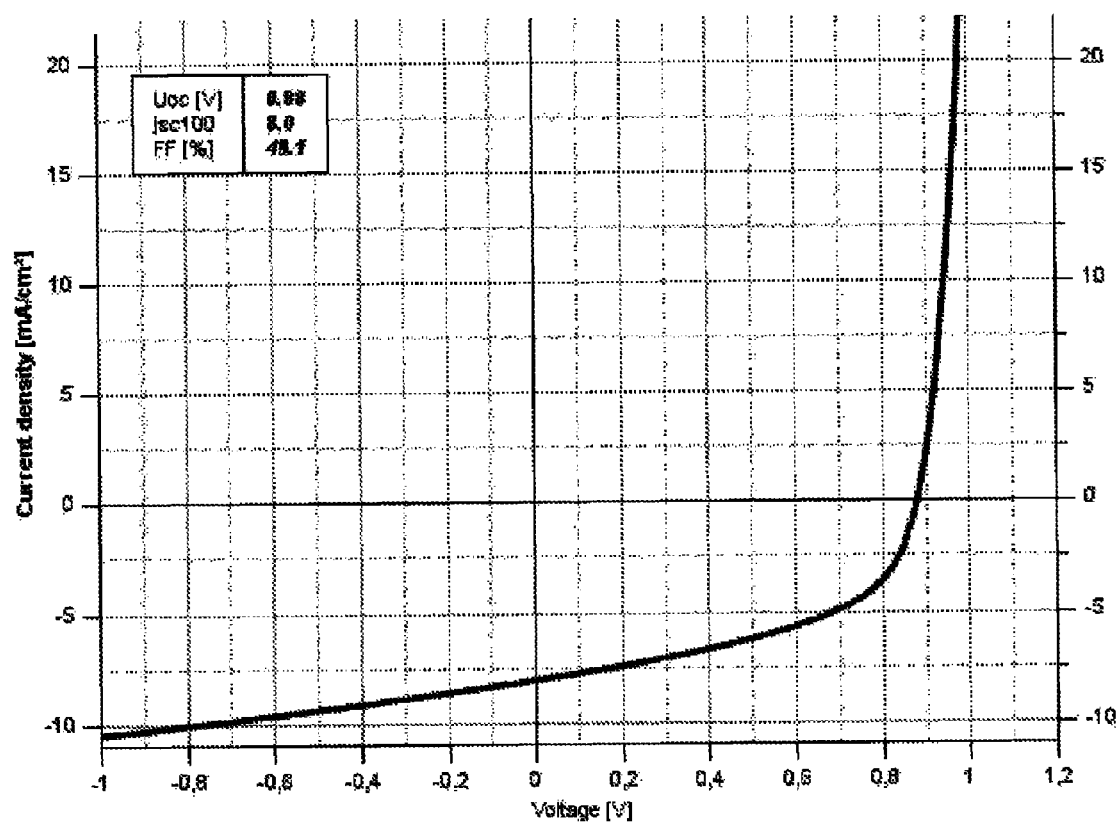

FIGS. 9A and 9B show a schematic diagram of an absorption spectrum of the compound and the current-voltage curve of this Mip cell comprising a mixed layer of compound DCV-TzPyTz-Pr2(3,3) with $C_{60}$. The most important parameters such as the fill factor FF, the open-circuit voltage $U_{oc}$ and the short-circuit current $j_{sc}$ show a functioning organic solar cell.

LIST OF REFERENCE NUMERALS

1 Substrate
2 Electrode
3 Transport layer system (ETL or HTL)
4 Organic light-sensitive layer system
5 Transport layer system (ETL or HTL)
6 Counterelectrode

The invention claimed is:
1. A compound of the general formula IIIa:

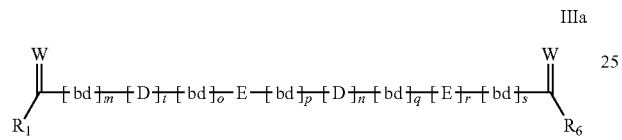

IIIa where each W is independently selected from $C(CN)_2$, CHCN, and C(CN)COOR' where R' is in each case selected from C1-C10 alkyl, C3-C10 aryl and C2-C8 heteroaryl,
$R_1$ and $R_6$ are each independently selected from H, C1-C30 alkyl, C1-C30 perfluoroalkyl, C3-C10 aryl, C2-C8-heteroaryl, and CN
where the D groups are selected from:

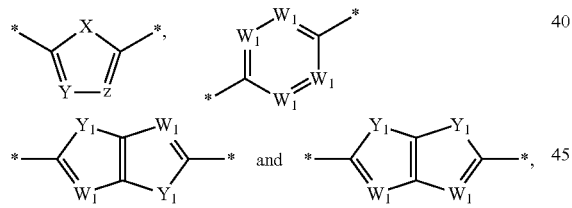

where
where $Y_1$ is selected from: O, S, Se, P(R), P(O)R, Si(RR'), C(RR') and N(R) and where R and R' are each independently selected from substituted and unsubstituted C1 to C30 alkyl, C3-C6 aryl and C3-C8 heteroaryl, and
$W_1$ is independently selected from: N and C—R where R is selected from hydrogen, halogen, and substituted and unsubstituted C1 to C30 alkyl, and
where each X is selected independently from O, NR', S, Se, where R' is selected from C1-C30 alkyl, C1-C10 aryl and C1-C8 heteroaryl,
each Y is independently selected from N and CR9 where R9=H, halogen, C1-C30 alkyl, C1-C30 alkenyl, C1-C30 alkynyl, each linear or branched, substituted or unsubstituted, OR', SR', $SiR'_3$, or $NR'_2$, where R' is selected from C1-C10 alkyl, C3-C10 aryl and C1-C8 heteroaryl,
each Z is independently selected from N and CR10 where R10=H, halogen, C1-C30 alkyl, C1-C30 alkenyl, C1-C30 alkynyl, each linear or branched, substituted or unsubstituted, OR', SR', $SiR'_3$, or $NR'_2$, where R' is selected from C1-C10 alkyl, C3-C10 aryl and C1-C8 heteroaryl,
or wherein R9 and R10 form a 5-membered or 6-membered ring,
where the E groups are selected from:

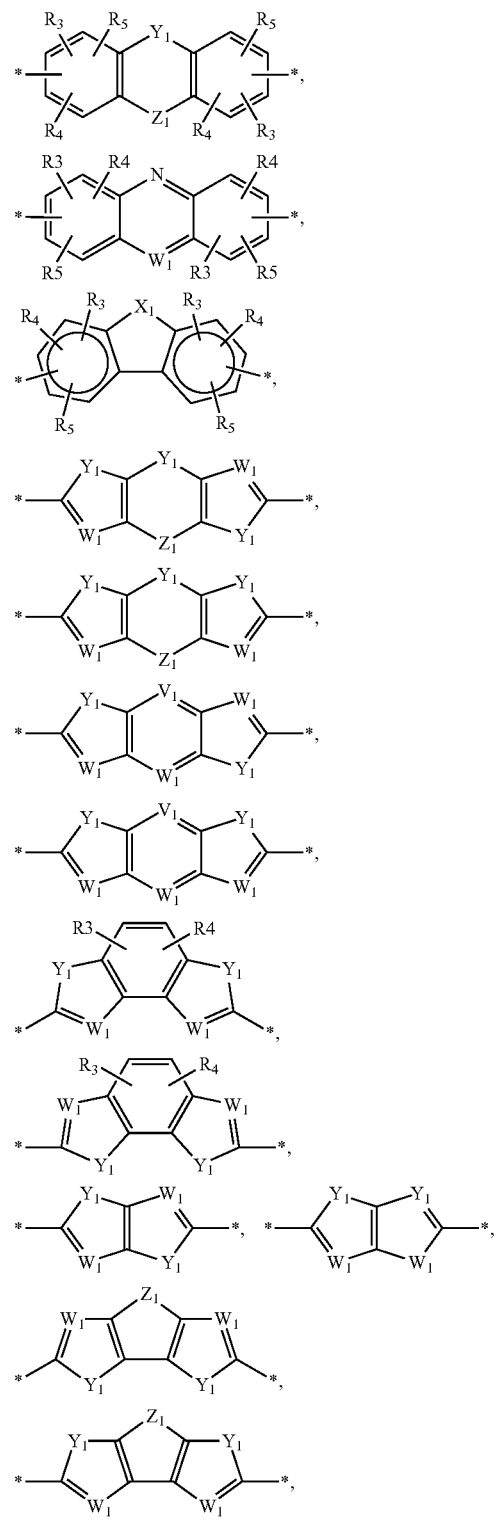

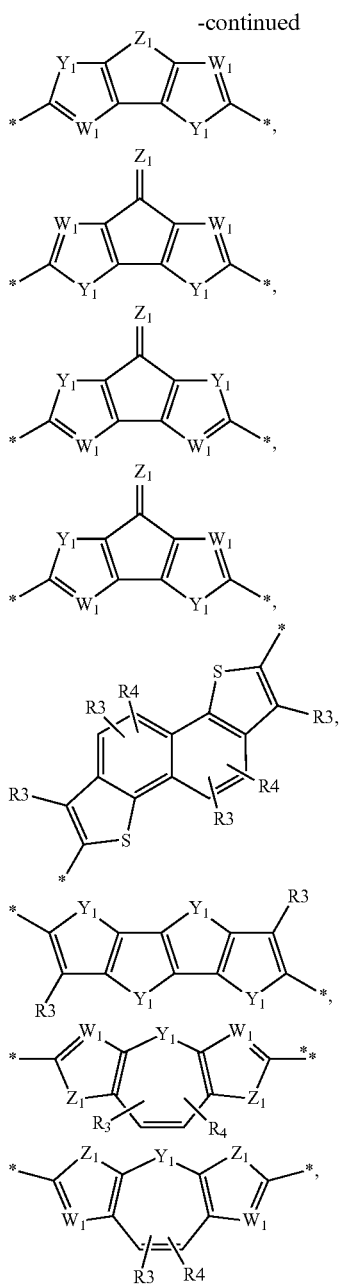

where $V_1$ and $W_1$ are each independently selected from:
N and C—R where R=H, halogen, C1-C30 alkyl, C1-C30 alkenyl, C1-C30 alkynyl, each linear or branched, substituted or unsubstituted, C3-C10 aryl or C1-C8 heteroaryl, substituted or unsubstituted, OR', SR', SiR'$_3$, or NR'$_2$, where R' is selected from C1-C10 alkyl, C1-C10 aryl and C1-C8 heteroaryl, $Y_1$ and $Z_1$ are each selected from:
O, S, Se, P(R), P(O)R, Si(RR'), C(RR') and N(R), where R and R' are each independently selected from H, linear or branched, substituted or unsubstituted C1-C30 alkyl, substituted or unsubstituted aryl, substituted or unsubstituted heteroaryl, COR', COOR' and OR', where R' is selected from C1-C30 alkyl, C3-C10 aryl and C1-C8 heteroaryl, and $X_1$ is selected from:
O, S, Se, P(R), P(O)R and Si(RR'), and R and R' are each independently selected from H, C1 to C20 alkyl, linear or branched, substituted or unsubstituted, C3 to C6 aryl or C3 to C8 heteroaryl, OR', SR', SiR'$_3$, and NR'$_2$, where R' is selected from C1-C10 alkyl, C3-C6 aryl and C3-C8 heteroaryl, and where R3, R4 and R5 are each independently H, C1 to C20 alkyl, linear or branched, substituted or unsubstituted, C3 to C6 aryl or C3 to C8 heteroaryl, OR', SR', SiR'$_3$, or NR'$_2$, where R' may be selected from C1-C10 alkyl, C3-C6 aryl and C3-C8 heteroaryl, bd is independently *—C=C—* or *—C≡C—*, n, m, o, p, q, r, s and t may each independently be 0 or 1, with the proviso that at least one parameter is 1, where one donor unit formed from the groups bd, E and D has at least 10 conjugated electrons and the bonds identified with the asterisk* indicate the bonds to further groups in the compounds.

2. A compound according to claim 1, wherein said compounds of the formula IIIa has point or mirror symmetry at least in relation to the main chain.

3. A compound according to claim 1 where r=s=0 and D is selected from

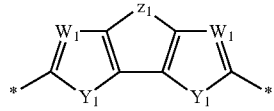

4. A compound according to claim 1, where the E group=

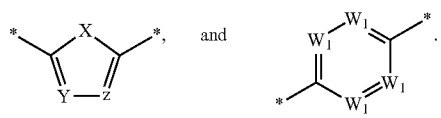

where $Y_1$=S and the D groups=

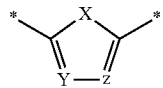

having the general formula:

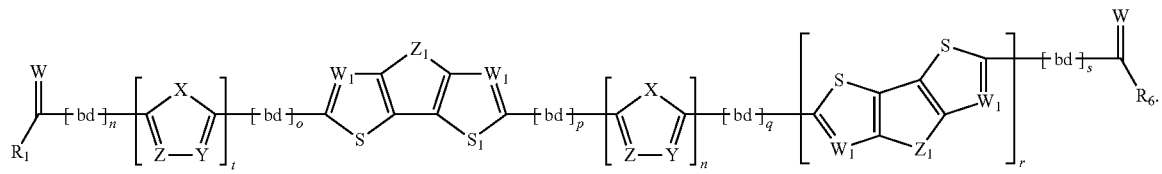

5. A compound according to claim 4 where m, r, s and q=0 having the general formula:

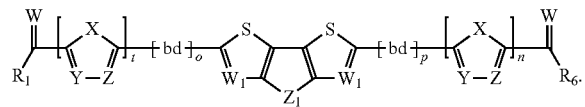

6. A compound according to claim 5 where o and p=0 and t and n=1 and $W_1$=C—R having the general formula:

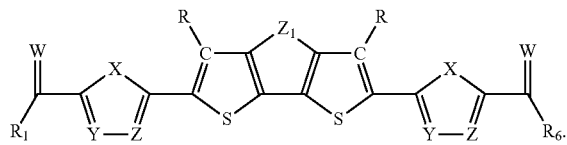

7. A compound according to claim 4 where t, m, o and s=0 and r=1 having the general formula:

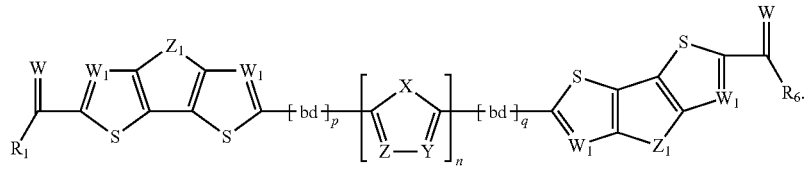

8. A compound according to claim 7 where p and q=0 and $W_1$=C—R having the general formula:

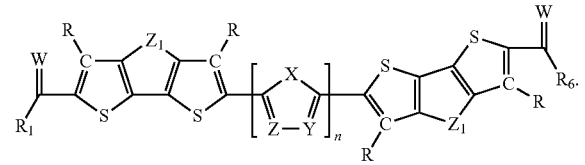

9. A compound according to claim 1 where D=

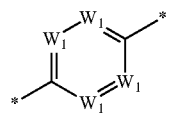

and E=

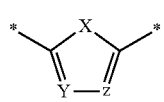

10. A compound according to claim 9 where m, r, s and q=0, $Y_1$=S and t and n each=1 having the general formula:

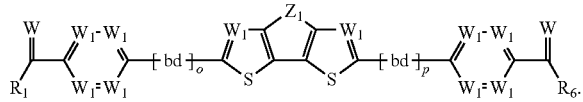

11. A compound according to claim 10 where o and p=0 and $W_1$=C—R.

12. A compound according to claim 1 where D=

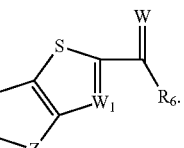

and E is selected from:

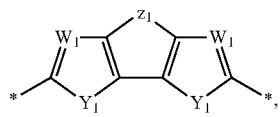, and

13. A compound according to claim 12 where m, q, r and s=0 and t and n each=1 having the general formula:

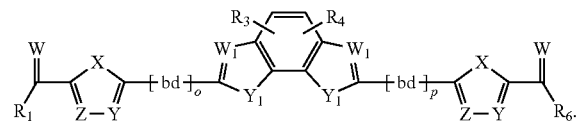

14. A compound according to claim 13 where X=S, and $Y_1$=S and $W_1$=C—R.

15. A compound according to claim 1, where m, t, n, o, q and s=0 and r=1, where E is selected from:

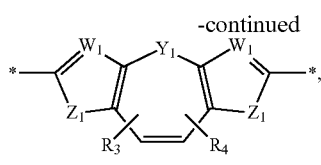

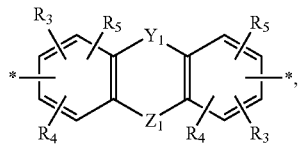

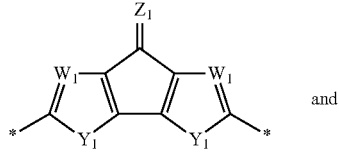
and

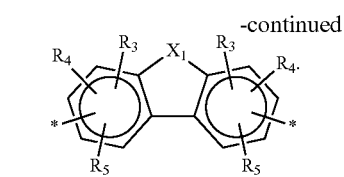

16. A compound according to claim 15, where additionally p=0.

17. A compound according to claim 6 wherein R9 and R10 form a 5-membered or 6-membered ring.

18. A compound according to claim 1, in which W is selected from: $C(CN)_2$, and CHCN, and R1 and R6 are each selected from: H and CN.

19. An optoelectronic component having an electrode and a counterelectrode and at least one organic light-sensitive layer between the electrode and the counterelectrode, wherein the organic light-sensitive layer comprises at least one compound according to claim 1.

20. A compound according to claim 1 wherein W is selected from $C(CN)_2$ and CHCN.

* * * * *